Figure 1:
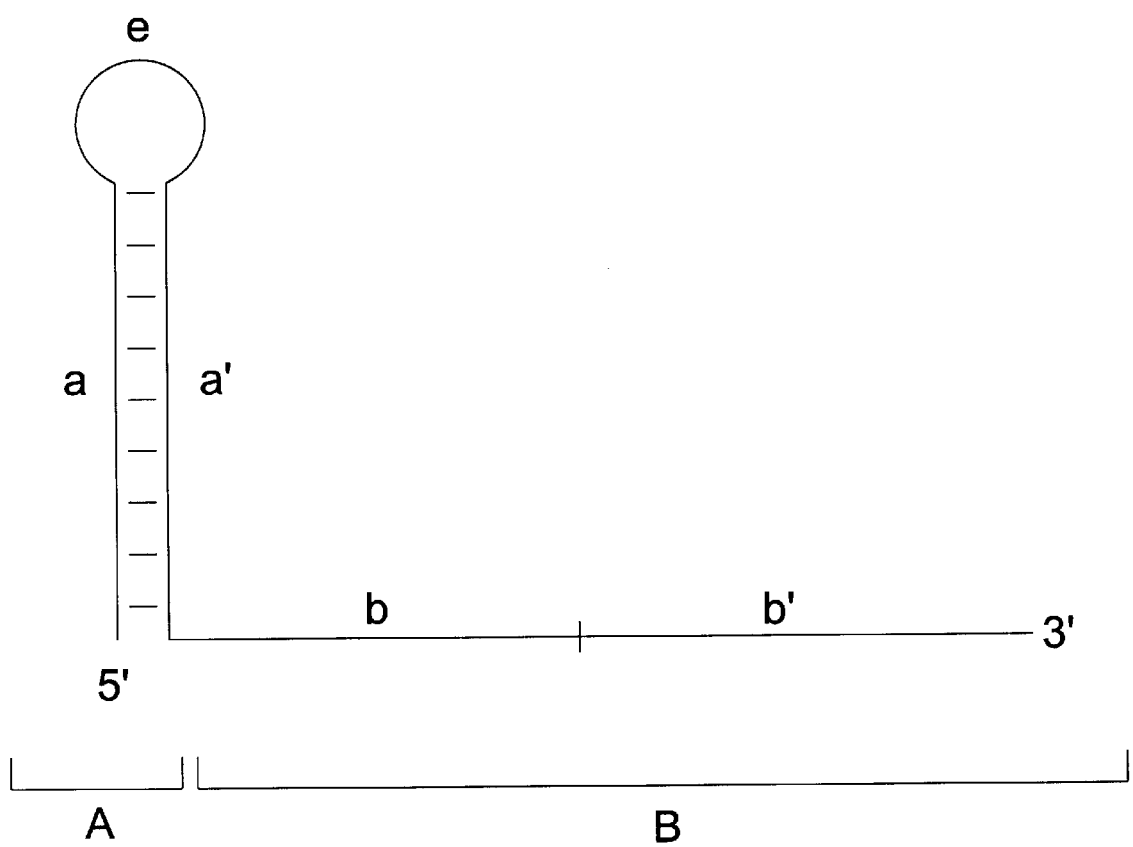

United States Patent [19]
Cleuziat et al.

[11] Patent Number: 5,874,260
[45] Date of Patent: Feb. 23, 1999

[54] OLIGONUCLEOTIDE WHICH CAN BE USED AS PRIMER IN A METHOD OF AMPLIFICATION BASED ON A REPLICATION ACCOMPANIED BY STRAND DISPLACEMENT

[75] Inventors: Philippe Cleuziat, Lyons; Francoise Guillou-Bonnici, Villeurbanne, both of France; Pierre Levasseur, Watertown, Mass.; Francois Mallet, Villeurbanne, France

[73] Assignee: Bio Merieux, Marcy L'Etoile, France

[21] Appl. No.: 549,211

[22] Filed: Oct. 27, 1995

[30] Foreign Application Priority Data

Oct. 28, 1994 [FR] France .................................. 94 13010

[51] Int. Cl.⁶ ...................................................... C12P 19/34
[52] U.S. Cl. ........................................ 435/91.2; 536/24.33
[58] Field of Search ................................ 455/6; 435/91.2; 536/24.33

[56] References Cited

U.S. PATENT DOCUMENTS

| | | | |
|---|---|---|---|
| 5,040,193 | 8/1991 | Leonowich et al. | 375/87 |
| 5,103,466 | 4/1992 | Bazes | 375/110 |
| 5,194,370 | 3/1993 | Berninger et al. | 435/6 |
| 5,369,003 | 11/1994 | Reischl et al. | 435/6 |
| 5,411,875 | 5/1995 | Jones | 435/91.2 |
| 5,474,916 | 12/1995 | Reischl et al. | |

FOREIGN PATENT DOCUMENTS

| | | | |
|---|---|---|---|
| 0 383 557 A1 | 8/1990 | European Pat. Off. | H04B 10/20 |
| 0395398 | 10/1990 | European Pat. Off. | |
| 0451591 | 10/1991 | European Pat. Off. | |
| 0530112 | 3/1993 | European Pat. Off. | |
| 0534345 | 3/1993 | European Pat. Off. | |
| 0543612 | 5/1993 | European Pat. Off. | |
| 0 614 281 A2 | 9/1994 | European Pat. Off. | H03L 7/081 |
| 4213029 | 4/1993 | Germany | |
| 93/05184 | 3/1993 | WIPO | |
| WO 93/17127 | 9/1993 | WIPO | |

OTHER PUBLICATIONS

G. Caetano–Anolies, "DNA Amplification Fingerprinting Using Arbitrary Mini–hairpin Oligonucleotide Primers", *Bio/Technology*, vol. 12, Jun. 1994, pp. 619–623.

G. Krupp et al., "Simplified in vitro synthesis of mutated RNA molecules", *Federation of European Biochemical Societies*, vol. 212, Feb. 1987, pp. 271–275.

W. Carpenter et al., "A Transcriptionally Amplified DNA Probe Assay with Ligatable Probes and Immunochemical Detection", *Clin. Chem.* vol. 39, No. 9, 1993, pp. 1934–1938.

*Primary Examiner*—Scott W. Houtteman
*Attorney, Agent, or Firm*—Oliff & Berridge, PLC

[57] ABSTRACT

Oligonucleotide comprising, from 5' to 3', a first portion comprising an upstream segment and a downstream segment forming a stem-loop structure, and a second portion not capable of self-pairing, in which the first portion comprises at least one blocking agent, capable of blocking the replication, by a polymerase, of the said oligonucleotide, such that at least one portion of the downstream segment is replicated and such that the upstream segment is replicated neither totally nor partially. This oligonucleotide can be used as primer in a process for the cyclic amplification of a target sequence of a nucleic acid.

19 Claims, 13 Drawing Sheets

DOUBLE-STRANDED NUCLEIC ACID

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 15..16
        ( D ) OTHER INFORMATION: /note= "N=3-amino-1,2-propanediol
            residue"

( x i ) SEQUENCE DESCRIPTION: SEQ ID NO:1:

```
TCCATCGCTT CGGGNNAACG AAGCGATGGA AGTAATTTAA TACGACTCAC TATAGAAAGA        60

GGATGGCATG ACAGTA                                                       76
```

( 2 ) INFORMATION FOR SEQ ID NO:2:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 15
        ( D ) OTHER INFORMATION: /note= "N=HEXAETHYLENE GLYCOL
            RESIDUE"

( x i ) SEQUENCE DESCRIPTION: SEQ ID NO:2:

```
TCCATCGCTT CGGGNAACGA AGCGATGGAA GTAATTTAAT ACGACTCACT ATAGAAAGAG        60

GATGGCATGA CAGTA                                                        75
```

( 2 ) INFORMATION FOR SEQ ID NO:3:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 15..16
        ( D ) OTHER INFORMATION: /note= "N=3-amino-1,2-propanediol
            residue"

( x i ) SEQUENCE DESCRIPTION: SEQ ID NO:3:

```
TCCATCGCTT CGGGNNAACG AAGCGATGGA AGTAATTTAA TACGACTCAC TATAGAAAGA        60

GTTGGCCGCA GTGTTAT                                                      77
```

( 2 ) INFORMATION FOR SEQ ID NO:4:

( i ) SEQUENCE CHARACTERISTICS:

(A) LENGTH: 76 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 15
(D) OTHER INFORMATION: /note= "N=HEXAETHYLENE GLYCOL RESIDUE"

(xi) SEQUENCE DESCRIPTION: SEQ ID NO:4:

TCCATCGCTT CGGGNAACGA AGCGATGGAA GTAATTTAAT ACGACTCACT ATAGAAAGAG 60

TTGGCCGCAG TGTTAT 76

(2) INFORMATION FOR SEQ ID NO:5:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 15..16
(D) OTHER INFORMATION: /note= "N=3-amino-1,2-propanediol residue"

(xi) SEQUENCE DESCRIPTION: SEQ ID NO:5:

TCCATCGCTT CGGGNNAACG AAGCGATGGA GGATGGCATG ACAGTA 46

(2) INFORMATION FOR SEQ ID NO:6:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 15
(D) OTHER INFORMATION: /note= "N=hexaethylene glycol residue"

(xi) SEQUENCE DESCRIPTION: SEQ ID NO:6:

TCCATCGCTT CGGGNAACGA AGCGATGGAG GATGGCATGA CAGTA 45

(2) INFORMATION FOR SEQ ID NO:7:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 15..16
(D) OTHER INFORMATION: /note= "N=3-amino-1,2-propanediol residue"

(xi) SEQUENCE DESCRIPTION: SEQ ID NO:7:

TCCATCGCTT CGGGNNAACG AAGCGATGGA GTTGGCCGCA GTGTTAT      47

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 15
        ( D ) OTHER INFORMATION: /note= "N=hexaethylene glycol
            residue"

( x i ) SEQUENCE DESCRIPTION: SEQ ID NO:8:

TCCATCGCTT CGGGNAACGA AGCGATGGAG TTGGCCGCAG TGTTAT      46

( 2 ) INFORMATION FOR SEQ ID NO:9:

( i ) SEQUENCE CHARACTERISTICS:
        ( A ) LENGTH: 861 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

ATGAGTATTC AACATTTCCG TGTCGCCCTT ATTCCCTTTT TTGCGGCATT TTGCCTTCCT      60
GTTTTTGCTC ACCCAGAAAC GCTGGTGAAA GTAAAAGATG CTGAAGATCA GTTGGGTGCA     120
CGAGTGGGTT ACATCGAACT GGATCTCAAC AGCGGTAAGA TCCTTGAGAG TTTTCGCCCC     180
GAAGAACGTT TTCCAATGAT GAGCACTTTT AAAGTTCTGC TATGTGGCGC GGTATTATCC     240
CGTGTTGACG CCGGGCAAGA GCAACTCGGT CGCCGCATAC ACTATTCTCA GAATGACTTG     300
GTTGAGTACT CACCAGTCAC AGAAAAGCAT CTTACGGATG CATGACAGT AAGAGAATTA     360
TGCAGTGCTG CCATAACCAT GAGTGATAAC ACTGCGGCCA ACTTACTTCT GACAACGATC     420
GGAGGACCGA AGGAGCTAAC CGCTTTTTTG CACAACATGG GGGATCATGT AACTCGCCTT     480
GATCGTTGGG AACCGGAGCT GAATGAAGCC ATACCAAACG ACGAGCGTGA CACCACGATG     540
CCTGCAGCAA TGGCAACAAC GTTGCGCAAA CTATTAACTG GCGAACTACT TACTCTAGCT     600
TCCCGGCAAC AATTAATAGA CTGGATGGAG GCGGATAAAG TTGCAGGACC ACTTCTGCGC     660
TCGGCCCTTC CGGCTGGCTG GTTTATTGCT GATAAATCTG GAGCCGGTGA GCGTGGGTCT     720
CGCGGTATCA TTGCAGCACT GGGGCCAGAT GGTAAGCCCT CCCGTATCGT AGTTATCTAC     780
ACGACGGGGA GTCAGGCAAC TATGGATGAA CGAAATAGAC AGATCGCTGA GATAGGTGCC     840
TCACTGATTA AGCATTGGTA A                                               861

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AATTCTAATA CGACTCACTA TAGGGAGATT ACCAATGCTT AATCA      45

( 2 ) INFORMATION FOR SEQ ID NO:11:

( i ) SEQUENCE CHARACTERISTICS:
         ( A ) LENGTH: 18 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:11:

ATGAGTATTC AACATTTC                                                                                       18

( 2 ) INFORMATION FOR SEQ ID NO:12:

( i ) SEQUENCE CHARACTERISTICS:
         ( A ) LENGTH: 100 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:12:

GTTGGCCGCA GTGTTACTAC TCATGGTTAT GGCAGCACTG CATAATTCTC TTACTGTCAT                                        60

GCCATCCGTA AGATGCTTTT CTGTGACTGG TGAGTACTCA                                                             100

( 2 ) INFORMATION FOR SEQ ID NO:13:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:13:

AGTACTCACC AGTCACA                                                                                       17

( 2 ) INFORMATION FOR SEQ ID NO:14:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:14:

GCACTGCATA ATTCTCT                                                                                       17

( 2 ) INFORMATION FOR SEQ ID NO:15:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:15:

CACTCATGGT TATGGCA                                                                                       17

( 2 ) INFORMATION FOR SEQ ID NO:16:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:16:

AATTAACCCT CACTAAAG    18

( 2 ) INFORMATION FOR SEQ ID NO:17:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

AATTCTAATA CGACTCACTA TAGGGAGACC CCGAAGAACG TTTTC    45

( 2 ) INFORMATION FOR SEQ ID NO:18:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

CTCCTTCGGT CCTCCGATC    19

( 2 ) INFORMATION FOR SEQ ID NO:19:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:19:

TAATACGACT CACTATAG    18

( 2 ) INFORMATION FOR SEQ ID NO:20:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

ATTTAGGTGA CACTATAG    18

( 2 ) INFORMATION FOR SEQ ID NO:21:

( i ) SEQUENCE CHARACTERISTICS:
    ( A ) LENGTH: 58 base pairs
    ( B ) TYPE: nucleic acid
    ( C ) STRANDEDNESS: single (D) TOPOLOGY: linear (i i) MOLECULE TYPE: DNA (genomic)

(i x) FEATURE:
    (A) NAME/KEY: misc_feature
    (B) LOCATION: 1,5,9..12,18..19
    (D) OTHER INFORMATION: /note= "N=i"

(x i) SEQUENCE DESCRIPTION: SEQ ID NO:21:

NATANATANN NNCATTTNNT AATACGACTC ACTATAGAAA GAGGATGGCA TGACAGTA      58

(2) INFORMATION FOR SEQ ID NO:22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:22:

TACTGTCATG CCATCC      16

(2) INFORMATION FOR SEQ ID NO:23:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:23:

TCTAATCCTG TTTGCTCCCC AGTAATTTAA TACGACTCAC TATAGAAAGA GGATGGCATG      60

ACAGTA      66

(2) INFORMATION FOR SEQ ID NO:24:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:24:

TCTAATCCTG TTTGCTCCCC AGTAATTTAA TACGACTCAC TATAGAAAGA GTTGGCCGCA      60

GTGTTAT      67

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:25:

TCTAATCCTG TTTGCTCCCC      20

(2) INFORMATION FOR SEQ ID NO:26:

(  i  ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:26:

```
AACGAAGCGA TGGA                                                              14
```

( 2 ) INFORMATION FOR SEQ ID NO:27:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:27:

```
AGAGAATTAT GCAGTGC                                                           17
```

( 2 ) INFORMATION FOR SEQ ID NO:28:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:28:

```
TGCCATAACC ATGAGTG                                                           17
```

( 2 ) INFORMATION FOR SEQ ID NO:29:

( i ) SEQUENCE CHARACTERISTICS:
  ( A ) LENGTH: 54 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 16..19
  ( D ) OTHER INFORMATION: /note= "N=a-thymidine nucleoside"

( x i ) SEQUENCE DESCRIPTION: SEQ ID NO:29:

```
CCAACCACTC ACTCCNNNNG GAGTGAGTGG TTGGTTACGG ATGGCATGAC AGTA                  54
```

( 2 ) INFORMATION FOR SEQ ID NO:30:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 33
  ( D ) OTHER INFORMATION: /note= "N=3-amino-1,2-propanediol
    residue"

( x i ) SEQUENCE DESCRIPTION: SEQ ID NO:30:

ATGACAGTAC GGTAGGAGGT AGCGAAGCTT TTNCTTCGCT ACCT 44

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16
        (D) OTHER INFORMATION: /note= "N=hexaethylene glycol residue"

(xi) SEQUENCE DESCRIPTION: SEQ ID NO:31:

CCAACCACTC ACTCCNGGAG TGAGTGGTTG GTTACGGATG GCATGACAGT A 51

(2) INFORMATION FOR SEQ ID NO:32:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 24
        (D) OTHER INFORMATION: /note= "N=3-amino-1,2-propanediol residue"

(xi) SEQUENCE DESCRIPTION: SEQ ID NO:32:

CCAACCACTC ACTCCGCCGG TAANGGCGGA GTGAGTGGTT GGTTACGGAT GGCATGACAG 60

TA 62

(2) INFORMATION FOR SEQ ID NO:33:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CCAACCACTC ACTCCTTTTG GAGTGAGTGG TTGGTTACGG ATGGCATGAC AGTA 54

(2) INFORMATION FOR SEQ ID NO:34:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "N=6-chloro-2-methoxyacridine"

(ix) FEATURE:

(A) NAME/KEY: misc_feature
(B) LOCATION: 17
(D) OTHER INFORMATION: /note= "N=hexaethylene glycol
    residue"

(x i) SEQUENCE DESCRIPTION: SEQ ID NO:34:

NCCAACCACT CACTCCNGGA GTGAGTGGTT GGTTACGGAT GGCATGACAG TA        52

(2) INFORMATION FOR SEQ ID NO:35:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1
    (D) OTHER INFORMATION: /note=
        " N=6-chloro-2-methoxyacridine"

(x i) SEQUENCE DESCRIPTION: SEQ ID NO:35:

NCCAACCACT CACTCCTTTT GGAGTGAGTG GTTGGTTACG GATGGCATGA CAGTA     55

(2) INFORMATION FOR SEQ ID NO:36:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

(x i) SEQUENCE DESCRIPTION: SEQ ID NO:36:

TAATACGACT CACTATAGGG AGACTCCTTC GGTCCTCCGA TCG                  43

(2) INFORMATION FOR SEQ ID NO:37:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(x i) SEQUENCE DESCRIPTION: SEQ ID NO:37:

GGATGGCATG GACAGTA                                               17

(2) INFORMATION FOR SEQ ID NO:38:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ii) MOLECULE TYPE: DNA (genomic)

(x i) SEQUENCE DESCRIPTION: SEQ ID NO:38:

TAATACGACT CACTATAGAA AGAGTTGGCC GCAGTGTTAT                      40

(2) INFORMATION FOR SEQ ID NO:39:

(i) SEQUENCE CHARACTERISTICS:
    (A) LENGTH: 35 base pairs

-continued

```
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:39:

GGAGTGAGTG  GTTGGTTACG  GATGGCATGA  CAGTA                                    3 5

( 2 ) INFORMATION FOR SEQ ID NO:40:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:40:

GGAGTGAGTG  GTT                                                              1 3

( 2 ) INFORMATION FOR SEQ ID NO:41:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:41:

AACGAAGCGA  TG                                                               1 2

( 2 ) INFORMATION FOR SEQ ID NO:42:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:42:

TTGGTATGGC  TTCATTCAGC                                                       2 0
```

OLIGONUCLEOTIDE WHICH CAN BE USED AS PRIMER IN A METHOD OF AMPLIFICATION BASED ON A REPLICATION ACCOMPANIED BY STRAND DISPLACEMENT

The present invention relates to oligonucleotides capable of forming stem-loop type structures having the property of not being fully recopiable by DNA or RNA polymerase and capable of serving as replication primers for these same enzymes. The invention also relates to a process for the amplification of nucleic acids with the aid of such primers.

It is often necessary, in technologies relating to nucleic acids and to genetic material, to determine if a gene, a gene portion or a nucleotide sequence is present in a living organism, in a cellular extract of this organism or in a biological sample.

The search for specific nucleotide sequences is of immense value, especially for the detection of pathogenic organisms, the determination of the presence of alleles, the detection of the presence of lesions in a host genome and the detection of the presence of a specific mRNA or of the modification of a cellular host. Genetic diseases such as Huntingdon's disease, Duchenne's myopathy, phenylketonuria and b-thalassemia can be diagnosed by analysing the DNA from individuals. Furthermore, the diagnosis or the identification of viruses, viroids, bacteria, fungi, protozoa or some other form of plant or animal life may be performed by hybridization experiments with nucleic probes.

In the few examples mentioned above, after having identified a sequence specific for an organism or a disease, it is necessary to extract the nucleic acids from a sample, and to determine whether this sequence is present. Numerous detection methods have been developed for this proposal. These methods, and particularly those which require the detection of polynucleotides, are based on the purine-pyrimidine pairing properties of the complementary nucleic acid strands in the DNA-DNA, DNA-RNA and RNA-RNA duplexes. This pairing process occurs through the formation of hydrogen bonds between the adenine-thymine (A-T) and guanine-cytosine (G-C) bases of the double-stranded DNA; adenine-uracil (A-U) base pairs can also form through hydrogen bonding in the DNA-RNA or RNA-RNA duplexes. The pairing of nucleic acid strands for the determination of the presence or of the absence of a given nucleic acid molecule is commonly called "hybridization of nucleic acids" or simply "hybridization".

For the implementation of the invention, it is generally necessary for one or more specific target sequences to have been previously identified. The most direct method of detecting the presence of a target sequence in a nucleic acid sample is to obtain a "probe" whose sequence is sufficiently complementary to a portion of the target nucleic acid to hybridize with it. The probe thus synthesized may be applied in a sample containing nucleic acids, and if the target sequence is present, the probe will hybridize and form a reaction product. In the absence of target sequence and by avoiding any nonspecific hybridization phenomenon, no reaction product will be formed. If the synthesized probe is coupled to a detectable marker, the reaction product may be detected by measuring the quantity of marker present. The Southern (Southern E. M., 1975, J. Mol. Biol., 98 : 503), or Northern type transfers, or the Dot-Blot technique or sandwich hybridization (Dunn, A. R. and Hassel, J. A., 1977. Cell, 12 : 23) constitute examples of methods which can be used.

The principal difficulty of this approach is, however, that it is not directly applicable to cases where the number of copies of the target sequence present in a sample is low. It is, in this case, difficult to distinguish a significant signal, that is to say to distinguish the specific attachment of a probe onto its target sequence from the nonspecific attachment of the probe onto a sequence different from the target sequence. One of the solutions to this problem consists in increasing the detection signal by an additional reaction intended to specifically multiply beforehand the number of copies of a nucleic acid fragment, termed target sequence, present in a sample. This technique is commonly called "amplification".

Several target amplification techniques are described in the literature. They are based mainly either on the repetition of cycles for synthesis of DNA by extension of nucleotide primers hybridized to the target sequence to be amplified using a DNA polymerase ("Polymerase Chain Reaction", termed PCR, U.S. Pat. Nos. 4,683,195; 4,683,202 and 4,800, 159; European Patent Application No. 0,201,184; "Ligase Chain Reaction", termed LCR, European Patent Application No. 0,320,308; "Repair Chain Reaction", termed RCR, International Patent Application No. WO 90/01069), or on the repetition of cycles for synthesis of RNA in vitro, by transcriptional reaction using a DNA- or RNA-dependent RNA polymerase whose activity is necessarily associated with a specific region termed promoter region, containing a sequence or a structure acting as promoter (technique termed TAS, which is described in International Patent Application No. WO 88/10315; "Self-Sustained Sequence Replication", termed 3SR, which is described in International Patent Application No. WO 90/06995 and European Patent Application No. 0,373,960; "Nucleic Acid Sequence-Based Amplification", termed NASBA, which is described in International Patent Application No. WO 91/02818 and European Patent Application No. 0,329,822; "Single Primer Sequence Replication", termed SPSR, which is described in U.S. Pat. No. 5,194,370 and "Ligation Activated Transcription", termed LAT, described in U.S. Pat. No. 5,194,370).

However, all these amplification techniques have at least one major disadvantage. In some cases (PCR, LCR or RCR), the most important disadvantage is the need to carry out numerous temperature cycles in order to dissociate the reaction products from the target. The carrying out of three successive temperature cycles constitutes a disadvantage for the automation of these techniques and increases considerably the reaction time necessary for the amplification. Another disadvantage of some amplification techniques is the limitation of the size of the amplification reaction product. Techniques such as RCR or LCR make it possible to amplify only the target sequence corresponding to the primers and to the nucleotide probes used in the amplification process. The nonspecific background noise (that is to say in the absence of the target) is also a serious disadvantage of techniques such as LCR. Another major disadvantage of some amplification techniques lies in the large number of enzyme activities involved in the amplification process. Methods derived from TAS, such as 3SR or NASBA, require at least four enzymatic activities (DNA-dependent DNA polymerase, RNA-dependent DNA polymerase, DNA-dependent RNA polymerase, RNase H), or even five in the case of LAT which uses, in addition, a DNA ligase. It is consequently very difficult to make these techniques efficient because of the difficulty of achieving reaction conditions which satisfy simultaneously these four or five enzymatic activities. Finally, while various amplification techniques use nuclease (exonuclease, endonuclease, RNase) activities as means for separating nucleic acid strands (European Patent Application No. 0,500,224), their use is, however, damaging because of the risk of degrading the target or the reaction product by unwanted activities sometimes present in nuclease preparations. Consequently, the activity of these nucleases must be rigorously measured, so as to maintain an equilibrium between the action of the different enzymes involved. In the light of these numerous limitations, other amplification methods, which are alternative to these methods, have been proposed.

The "Strand Displacement Amplification" method, termed SDA, which is described in U.S. Pat. No. 5,270,184, allows an isothermal multiplication (37° C.) of a target DNA sequence by means of an appropriate restriction enzyme and of a DNA-dependent DNA polymerase lacking exonuclease activity (Walker et al., 1992, Proc. Natl. Acad. Sci. USA 89 : 392–396). It is based on the hybridization of oligonucleotide primers containing a sequence for recognition of a restriction enzyme at their 5' end. These primers are extended using DNA polymerase in the presence of at least one modified nucleotide (5'[-thio]dNTP). The digestion of the DNA with the restriction endonuclease causes the cleavage of the strand corresponding to the primer, leaving intact the modified complementary strand. DNA polymerase can then extend the primers generated and releases a DNA strand into the reaction medium by virtue of the strand displacement property of the DNA polymerase. This released strand can bind a new primer containing a restriction enzyme binding sequence and the cycle can start again. A method similar to STD, using an exonuclease activity instead of an endonuclease, called "exonuclease-mediated strand displacement amplification", is described in European Patent Application No. 0,500,224.

However, these methods too have disadvantages affecting their efficiency. Thus, they are limited by the type of target sequence to be amplified, since this sequence should not contain a restriction site corresponding to the endonuclease used in the process. It is therefore essential to know, if not the nucleic sequence of the fragment to be amplified, at least the restriction map of the said fragment. In addition, this disadvantage is increased by the choice of restriction endonucleases which is restricted to those having the capacity to cleave a hemiphosphorothioate recognition site and more generally sites containing modified nucleotides. In addition to the disadvantages linked to the chemical synthesis of the modified nucleotides, this amplification process has a limited yield because of the low efficiency of the enzymatic incorporation of the modified nucleotides.

Another isothermal amplification technique using, like PCR, two primers and a DNA polymerase has been described (U.S. Pat. No. 5,223,414). This technique uses the protein Rec A to form a complex between a first nucleotide primer and a 3' end of a nucleic acid strand and between a second primer and the 3' end of the strand complementary to this nucleic acid, in the presence of ATP. The complexes thus produced are then exposed to a DNA polymerase and to deoxyribonucleoside triphosphates. Several amplification cycles can then be performed under isothermal conditions. However, the amplification yield obtained is lower than that of PCR because the stage for separating the complementary strands from nucleic acids involves the process of recombination which is slower and more unpredictable than thermal denaturation. Furthermore, this method is based on the use of a protein (Rec A) together with a polymerase, which makes its optimization difficult.

Some amplification techniques involve primers or nucleic probes having a specific structure. Thus, in the case of the so-called LAT method (U.S. Pat. No. 5,194,370), the amplification of the target sequences, based on transcription, depends on the introduction, by ligation, of a stem-loop structure of DNA nature comprising, within the sequence forming the pin, a functional promoter for an RNA polymerase. In addition, the 3' end of the oligonucleotide carrying the stem-loop structure is blocked and consequently cannot serve as primer for a DNA polymerase. Other studies describe a similar use of a promoter sequence contained in a stem-loop type structure (European Patent Applications Nos. 0,451,591; 0,534,345; German Patent Application No. 42 13 029; Carpenter et al., 1993, Clin. Chem. 39 : 1934–1938; Krupp and Söll, 1987, FEBS Lett. 2 : 271–275). PCT Patent Application No. WO 93/17127 describes the use of oligonucleotides of DNA nature which form a stem-loop structure, ligated to the ends of the DNA target, in a PCR type amplification procedure using a single primer. European Patent Application No. 0,530,112 describes an amplification technique using the collaboration of a replication origin and an inverted repeat sequence capable of forming a stem-loop structure. The use of primers containing a stem-loop ministructure has also been described by Caetano and Gresshoff (1994, Bio/Technology 12 : 619–623). The use of these arbitrarily defined primers, but having a mini stem-loop, coupled with the PCR amplification technique, makes it possible to obtain a large number of amplified nucleic acid fragments which are heterogeneous in size and which require an electrophoretic separation stage in order to produce genetic fingerprints.

The different processes described above use specific oligonucleotides which may have a stem-loop structure, solely for the purpose either of introducing, in a single stage, a functional promoter upstream of the sequence to be amplified, or to allow the hybridization of specific primers in the loop located upstream of the target sequence followed by amplification, by primer extension, as in the case of PCR. Thus, none of these amplification techniques makes it possible to escape the various disadvantages of the other techniques mentioned above.

Given the above analysis, the design of new amplification methods appears to be desirable and the subject of the present invention is especially a method for the cyclic amplification of a target nucleotide sequence, capable of operating isothermally, and having the advantage of using only one nucleic acid polymerase in the presence of nucleoside triphosphates.

In the present application, the expression "upstream" designates a region situated on the side of the 5' end of the nucleic acid or of the polynucleotide sequence in question, and the expression "downstream" designates a region situated on the side of the 3' end of the said nucleic acid or of the said polynucleotide sequence.

Sequence homologous to another sequence designates a sequence capable of hybridizing with a sequence which is strictly complementary to the said other sequence.

"Self-paired" nucleic acid molecule designates a molecule in which at least one constituent nucleic sequence is hybridized with a nucleic sequence of the same nucleic acid molecule; this is in this case referred to as self-pairing or intramolecular pairing in contrast to intermolecular pairing which involves two separate nucleic acid molecules.

The term "nucleoside triphosphates" (NTP) designates either deoxyribonucleoside triphosphates (dNTP) and/or ribonucleoside triphosphates (rNTP).

The terms "nucleic acid fragment", "nucleic acid segment", "nucleic acid region" or "oligonucleotide" as used in the present application designate a natural DNA or RNA fragment, a natural or synthetic polynucleotide, which may optionally contain at least one modified base such as inosine, 5-methyldeoxycytidine, 5-dimethylaminodeoxyuridine, deoxyuridine, 2,6-diaminopurine, 5-bromodeoxyuridine, pseudouridine, pseudoisocytidine or any other modified base allowing hybridization. This polynucleotide may also be modified at the level of the intranucleotide bond (such as for example the phosphorothioate, H-phosphonate and alkyl phosphonate bonds), at the level of the backbone as is the case for example for the alpha-oligonucleotides (French Patent No. 2,607,507) or the PNAs (Egholm et al., 1992, J. Am. Chem. Soc. 114 : 1895–1897). In a modified polynucleotide, several of the modifications which have just been mentioned may be present in combination.

The term "nucleic sequence" designates a precise linkage of nucleotides, modified or otherwise, which make it possible to define a fragment, a segment or a region of nucleic acid, as defined above.

The term "primer" designates a molecule comprising a single-stranded oligonucleotide structure composed of at least five nucleotides. These nucleotides may be deoxyribonucleotides and/or ribonucleotides. These nucleotides may be modified as described above in the paragraph relating to the description of the term "nucleic acid fragment". The oligonucleotide primers, once hybridized to a substantially complementary nucleic acid sequence (DNA, RNA or chimeric DNA-RNA molecule), constitute substrates for polymerases. The oligonucleotide primers hybridized to a nucleic acid sequence have the property of binding a polymerase to their 3'OH end. The polymerase may then extend the primer from its 3'OH end, in the presence of suitable nucleotides, thus leading to the synthesis of a strand complementary to the template sequence to which the said primer is hybridized. A primer may also be produced by hybridization of the end of a single-stranded nucleic acid sequence onto itself, leading especially to the formation of secondary structures termed hair pins or stem-loops.

"Stem-loop" structure designates any secondary structure involving at least a nucleotide portion within which a strand of a nucleic acid sequence, via intramolecular hydrogen bonds, with another portion of the same nucleic acid molecule in order to constitute a "self-paired" region termed "pin" of double-stranded nature and an unpaired "loop" region located at one end of the said pin. When the length of the loop is zero, it produces the special case of stem-loop called "hair pin" or palindrome. Such "stem-loop" structures may form especially if a nucleotide sequence has two inverted repeat sequences separated, for example, by at least one nucleotide or by an arm of hydrocarbon nature.

"Blocking agent" refers to an agent capable of blocking the replication of a nucleic acid template by a nucleic acid polymerase (DNA polymerase, RNA polymerase, reverse transcriptase or replicase). Such agents are known. A blocking agent may be a nucleic compound (for example a modified nucleotide), or a non-nucleic compound, which is not recognized as template by the relevant polymerase. The blocking agent may be a hydrocarbon arm inserted between two nucleotides of the nucleic template at the site where it is desired to stop the replication. The expression "hydrocarbon arm" means here "essentially hydrocarbon arm": it is for example a polymethylene arm which may be inserted between two nucleotides, for example by the reaction of a diol or of a diamine (see the experimental section below). Such a polymethylene group may contain substituents or may be interrupted by one or more oxygen, sulphur or nitrogen heteroatoms for example.

"Replication" refers to any reaction catalysed by a nucleic acid polymerase, which results in the copy of a nucleic template, generally in the form of its complementary sequence. The polymerase is especially a DNA polymerase, an RNA polymerase, a reverse transcriptase or a replicase.

"Strand displacement activity" designates a phenomenon by which a biological, chemical or physical agent, for example a DNA polymerase, causes the gradual dissociation of a nucleic acid from its complementary strand with which it was paired, in conjunction with the neosynthesis of a nucleic acid complementary to the said complementary strand (template). The strand displacement starts at the 5' end of the nucleic acid thus displaced and continues in the 5'→3' direction whereas the neosynthesis of nucleic acid continues immediately upstream of the displacement site. The neosynthesized nucleic acid (forming a duplex with the template) and the displaced nucleic acid obtained (in the form of a single strand) generally have the same nucleotide sequence which is complementary to the template nucleic acid strand. The strand displacement activity may be present on the same molecule as that having the nucleic acid synthesis activity, and particularly the DNA synthesis, or it may be a separate and independent activity. DNA polymerases such as $E.$ $coli$ DNA polymerase, the Klenow fragment of DNA polymerase I, the T7 or T5 bacteriophage DNA polymerase, the HIV virus reverse transcriptase are enzymes which possess both the polymerase activity and the strand displacement activity. Agents such as helicases may be used in conjunction with inducing agents which do not possess strand displacement activity, in order to produce the strand displacement effect, that is to say the displacement of a nucleic acid coupled with the synthesis of a nucleic acid of the same sequence. Likewise, proteins such as Rec A or the Single Strand Binding Protein from $E.$ $coli$ or from another organism may be used to produce or enhance the strand displacement, in conjunction with other inducers. For further details and a discussion of strand displacement, Kornberg and Baker (1992, DNA Replication, 2nd Edition, p. 113–225, Freeman, New York) may be consulted. The strand displacement capacity allows especially the opening of a stem-loop type structure, in conjunction with the synthesis of at least a portion of this stem-loop type structure.

"Promoter" for an RNA polymerase designates a sequence or a structure capable of directing the initiation of transcription. The promoter sequences (in the form of a double strand) of different types of RNA polymerases are well known. In addition to the natural promoters for RNA polymerases, it is also possible to use shortened sequences derived from the natural promoters and having retained their functionality. Other structures capable of initiating transcription are for example "bubbles" or "loops" as described by Møllegaard et al. (1994, Proc. Natl. Acad. Sci. USA 91 : 3892–3895) and Alyar et al. (1994, J. Biol. Chem. 269 : 13179–13184).

"Sense" sequence of a promoter for RNA polymerase designates the sequence of the strand of the said promoter (double strand) whose 3' end is contiguous to the site of initiation of transcription which is defined by the same promoter.

"Antisense" sequence of a promoter for RNA polymerase designates the sequence of the strand of the said promoter (double strand) whose 5' end is contiguous to the nucleotide complementary to the site of initiation of transcription which is defined by the same promoter.

The subject of the invention is therefore an oligonucleotide comprising, from its 5' end to its 3' end:
  a first portion capable of self-pairing in order to form a stem-loop structure comprising an upstream segment and a downstream segment which are paired,
  and a second portion not capable of self-pairing, characterized in that the said first portion comprises at least one blocking agent capable of blocking the replication, by a polymerase, of the said oligonucleotide, such that at least a portion of the downstream segment is replicated and such that the upstream segment is replicated neither totally nor partially.

The blocking agent is for example such that the portion of the downstream segment capable of being replicated has a length of at least 2 nucleotides, and in particular of at least 3 nucleotides, or of at least 5 nucleotides.

The downstream end of the upstream segment and the upstream end of the downstream segment of the oligonucleotide may be linked by a nucleic or non-nucleic loop.

The upstream and downstream segments may each contain from 2 to 30, and in particular from 3 to 15 nucleotides.

The blocking agent comprises, for example, at least one modified nucleotide which is non-recopiable by a polymerase, or one hydrocarbon arm. The loop may contain the blocking agent.

The oligonucleotide may contain, between the first and second portions, a third portion containing the sense sequence of a promoter for an RNA polymerase.

According to a specific embodiment, the oligonucleotide of the invention is characterized in that the said second portion contains from 5 to 40 nucleotides.

The oligonucleotide of the invention may be used as primer in a process for the amplification of a target sequence of a nucleic acid, the said target sequence comprising a downstream sequence of at least 5 nucleotides, and in this case the said second portion contains at its 3' end a sequence capable of hybridizing with the said downstream sequence of the target.

The invention also relates to a process for the cyclic amplification of a target sequence of a nucleic acid, the said target sequence comprising at its 5' end an upstream region and at its 3' end a downstream region, comprising the stages consisting of:

obtaining a single-stranded polynucleotide comprising a first segment corresponding to the target sequence to be amplified, a second segment situated upstream of the 5' end of the first segment and a third segment situated downstream of the 3' end of the first segment, the said second segment of the said single-stranded polynucleotide being homologous to the said first portion of an oligonucleotide as defined above, and the said third segment of the said single-stranded polynucleotide having any sequence, exposing the said polynucleotide to:
(a) a first primer as defined above, capable of hybridizing with the downstream region of the target sequence, it being understood that at least the downstream portion of the downstream segment of the first portion of the first primer is complementary to the third segment of the single-stranded polynucleotide, optionally a second primer as defined above, capable of hybridizing with a downstream region of the sequence complementary to the target sequence, this downstream region being complementary to the said upstream region of the target sequence, it being understood that the first portion of the second primer is that of which the second segment of the said single-stranded polynucleotide is the homologue,
(b) a third primer whose sequence is homologous to at least a downstream portion of the sequence of the downstream segment of the said first portion of the first primer,
(c) a fourth primer whose sequence is homologous to at least a portion of the sequence of the downstream segment of the said first portion constituting the said second segment of the said single-stranded polynucleotide,
and (d) an enzymatic system containing at least an activity for replicating the said nucleic acid and a strand displacement activity,
and incubating the mixture obtained under conditions allowing the hybridization and the functioning of the said enzymatic activities.

In a specific embodiment of this process, the first primer may contain the sense sequence of a promoter, as mentioned above, and the process is then characterized in that the said single-stranded polynucleotide contains, between its first segment and its third segment, a fourth segment complementary to the said sense sequence contained in the first primer, and in that the said enzymatic system contains, in addition, an RNA polymerase activity under the control of the said promoter.

According to another specific embodiment which is not exclusive of the preceding specific embodiment, the second primer is present and also contains a sense sequence of a promoter, and the process is then characterized in that the said single-stranded polynucleotide contains, between its first segment and its second segment, an additional segment whose sequence is that of the sense sequence contained in the second primer, and in that the said system contains, in addition, an RNA polymerase activity under the control of the said promoter corresponding to this sense sequence contained in the second primer.

Specific embodiments will now be described with reference, where appropriate, to the accompanying drawings in which:

FIG. 1 describes an oligonucleotide according to the invention composed of a sequence capable of forming a stem-loop self-paired type structure and containing at least one agent blocking extension by a nucleic acid polymerase. The vertical lines, segments (a) and (a'), represent a nucleic acid sequence belonging to the pin (self-paired region), and the portion in the form of an arc of a circle a structure of nucleic and/or hydrocarbon nature forming the loop, segment (e). The discontinuous fine horizontal lines symbolize the hydrogen bonds formed between the complementary nucleotides hybridized within the pin. The polarity of the nucleic acids is indicated by their 5' and 3' ends.

Figure 2:
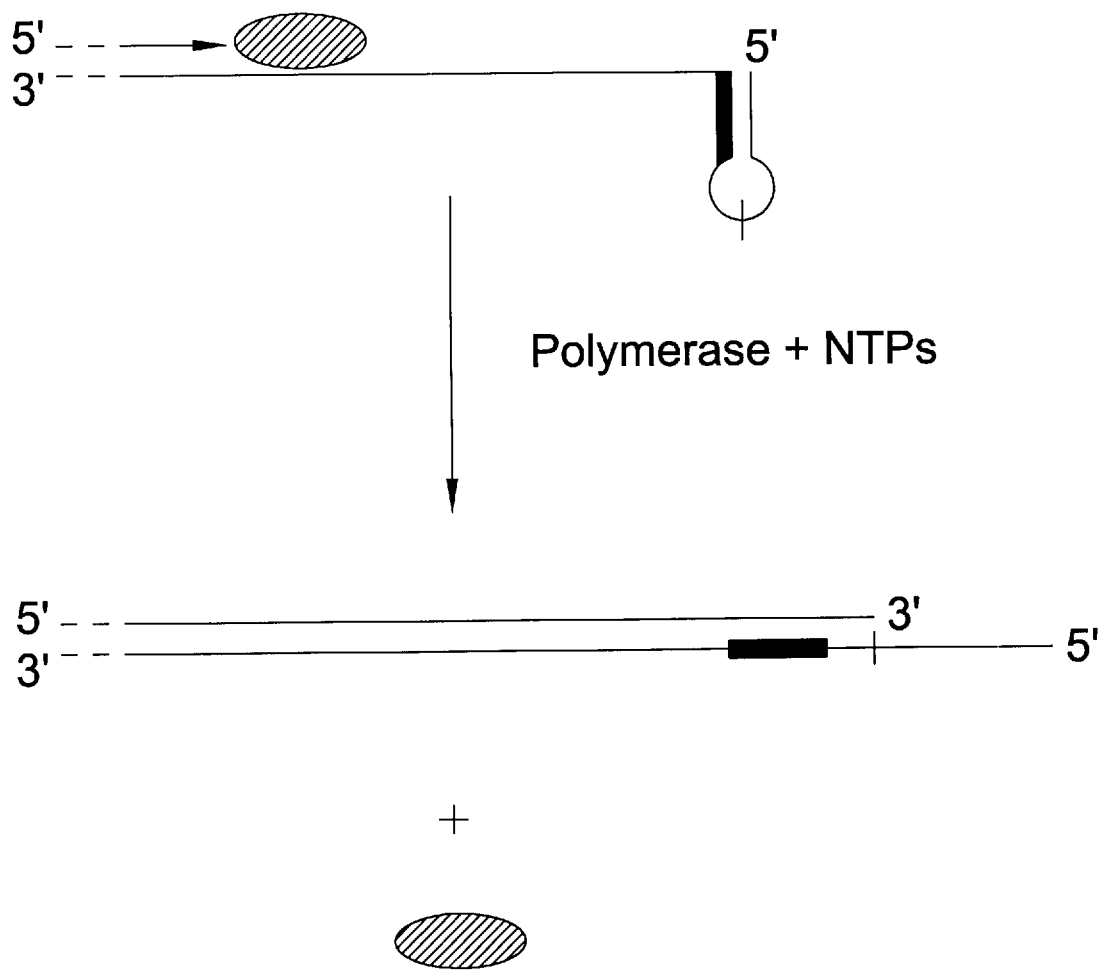

FIG. 2 describes the replication of a molecule comprising a stem-loop type structure and containing at least one agent blocking extension by a nucleic acid polymerase, with the aid for example of a DNA polymerase or an RNA polymerase (which are DNA and/or RNA dependent) in the presence of deoxyribonucleoside triphosphates (dNTPs) or of ribonucleoside triphosphates (rNTPs), respectively. The replication occurs for example by extending from 5' to 3' an oligonucleotide primer hybridized on the side of the 3' end of a template nucleic acid containing a stem-loop type structure. The straight lines represent a nucleic acid sequence and the portion in the form of an arc of a circle a structure forming the loop. The transverse line situated in the region of the loop designates the site from which the replication of the stem-loop becomes blocked. This results in a detachment of the polymerase (symbolized by the shaded ellipse) from its template. The highly thickened segment indicates the region of the pin recopied by the polymerase. The dotted lines represent the undefined ends of the nucleic acids.

Figure 3:
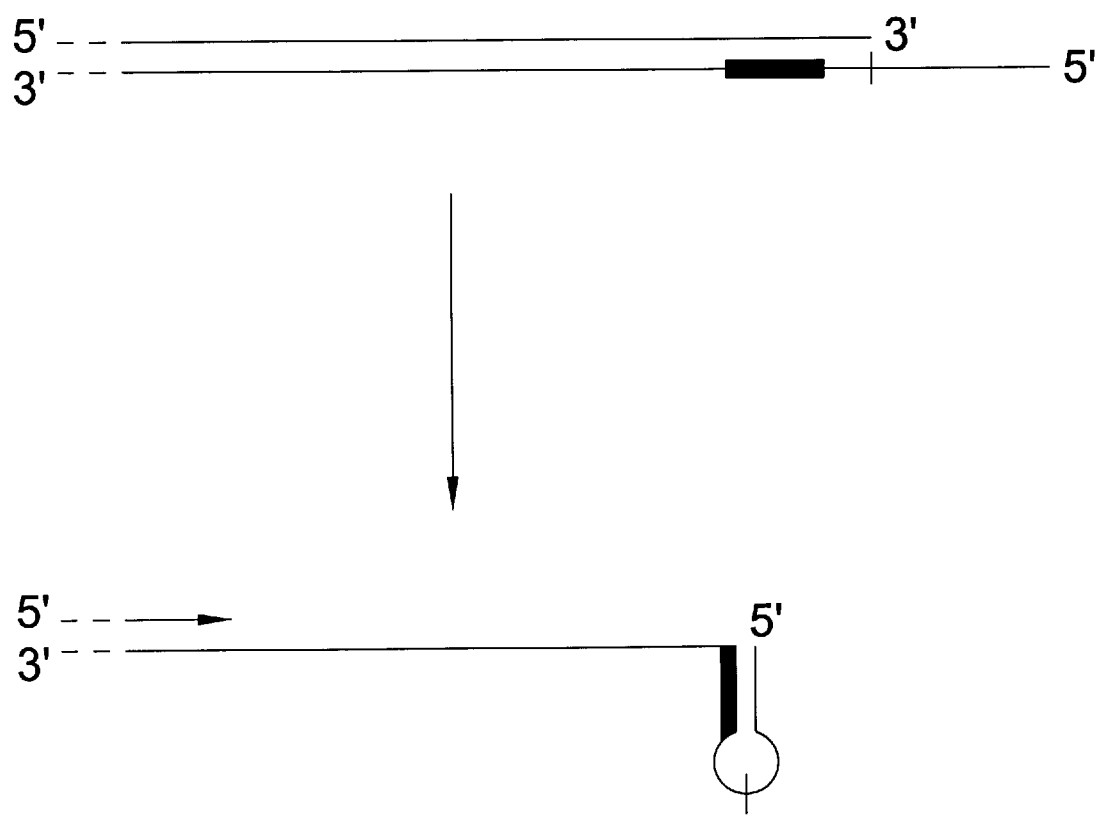

FIG. 3 describes how, by displacing the thermodynamic equilibrium, it is possible to obtain the A portion of the oligonucleotides in the form of a stem-loop self-paired molecular structure from a duplex molecule. The straight lines represent a nucleic acid sequence and the portion in the form of an arc of a circle a structure forming a loop. The short transverse line drawn in the region of the loop designates the site beyond which the replication of the stem-loop can no longer occur. The highly thickened line indicates the region of the pin recopied by polymerase. The dotted lines represent the undefined ends of the nucleic acids.

Figure 4A:
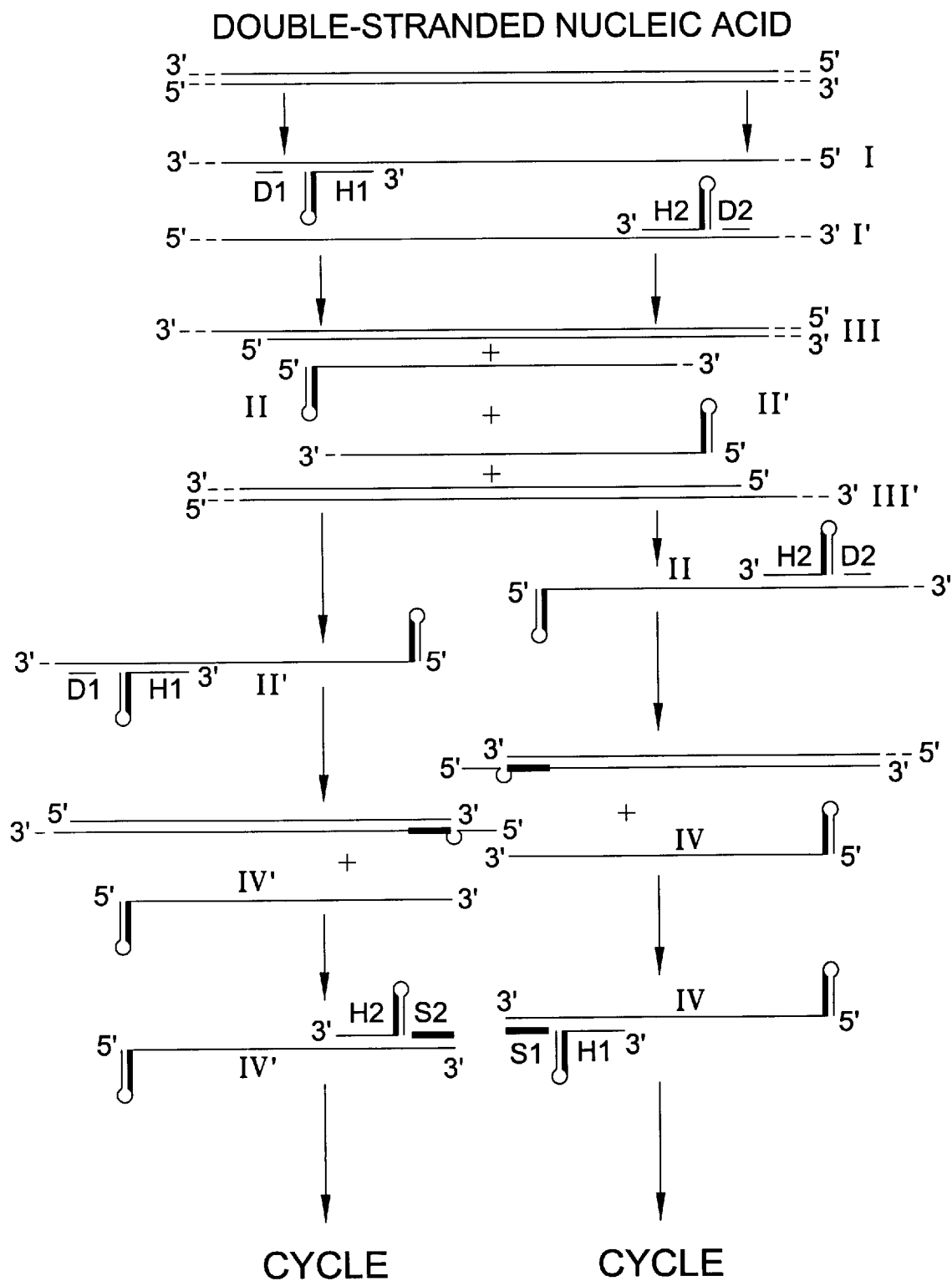
Figure 4B:
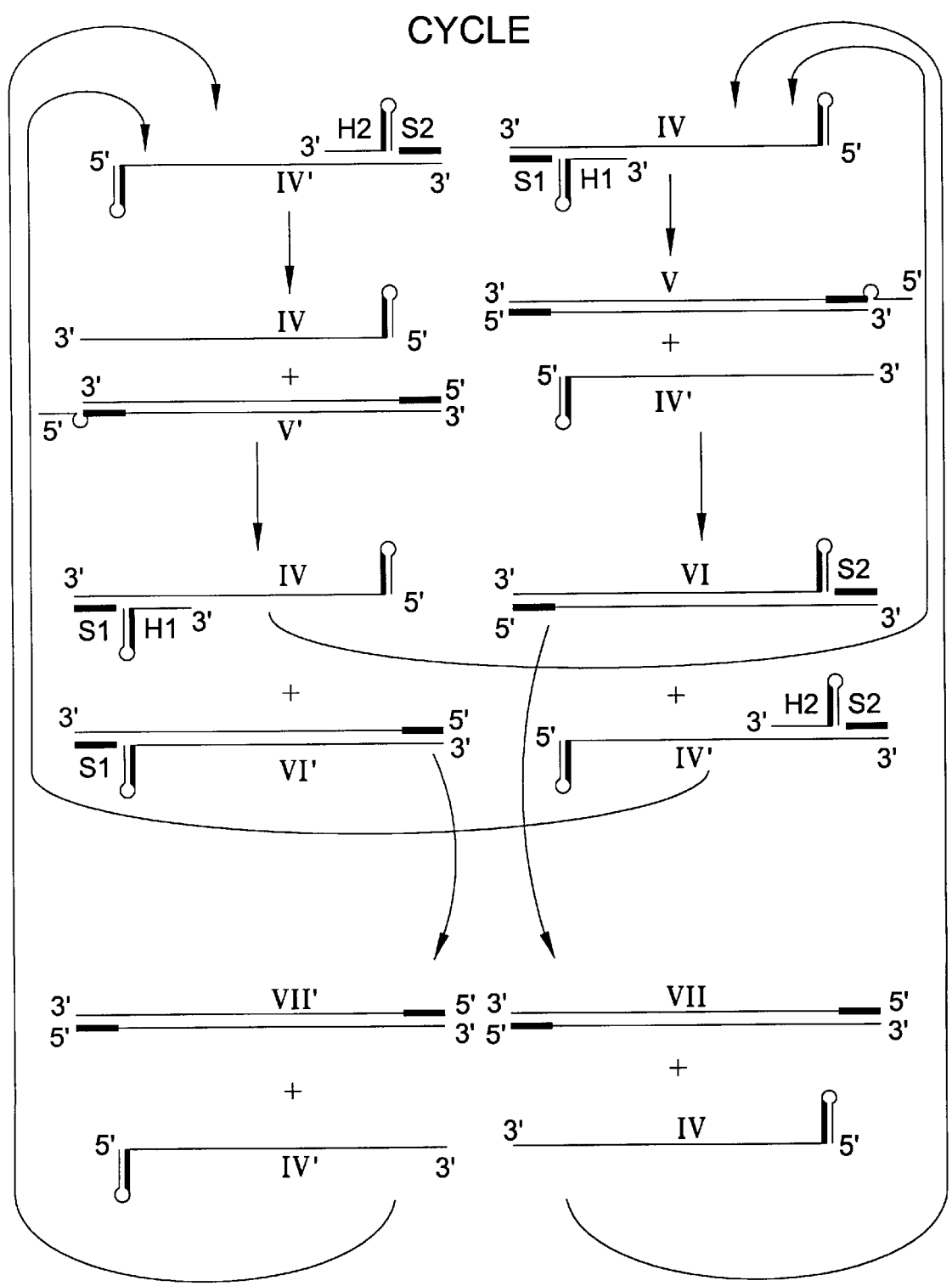

FIGS. 4A and 4B schematically represent a special case of amplification, in accordance with the invention, of nucleic acids using an oligonucleotide comprising a stem-loop structure. The straight lines represent a nucleic acid sequence and the portion in the form of an arc of a circle a structure forming the loop. The highly thickened segment indicates the region of the pin recopied by polymerase, as indicated in relation to FIG. 3.

Figure 5A:
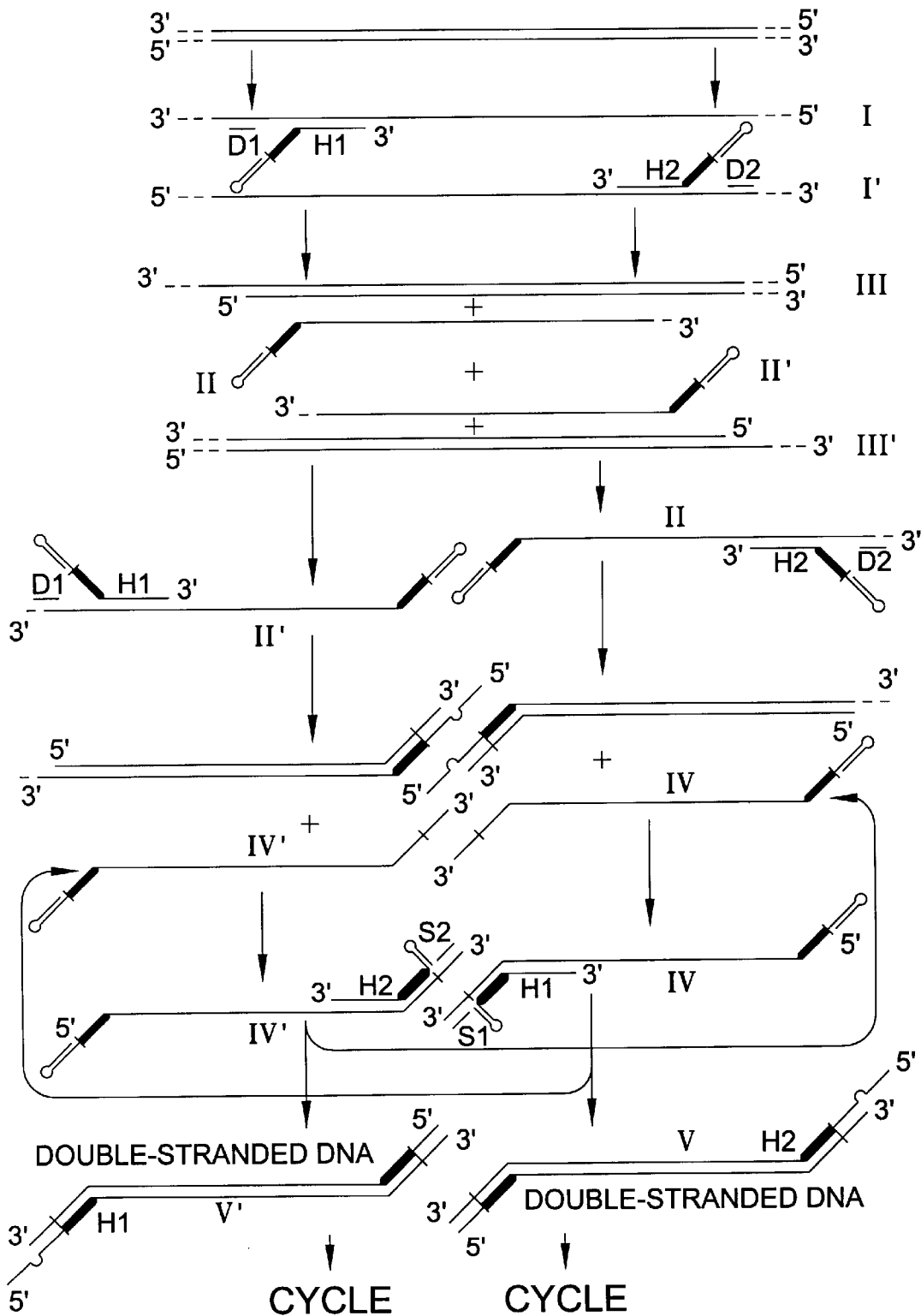
Figure 5B:
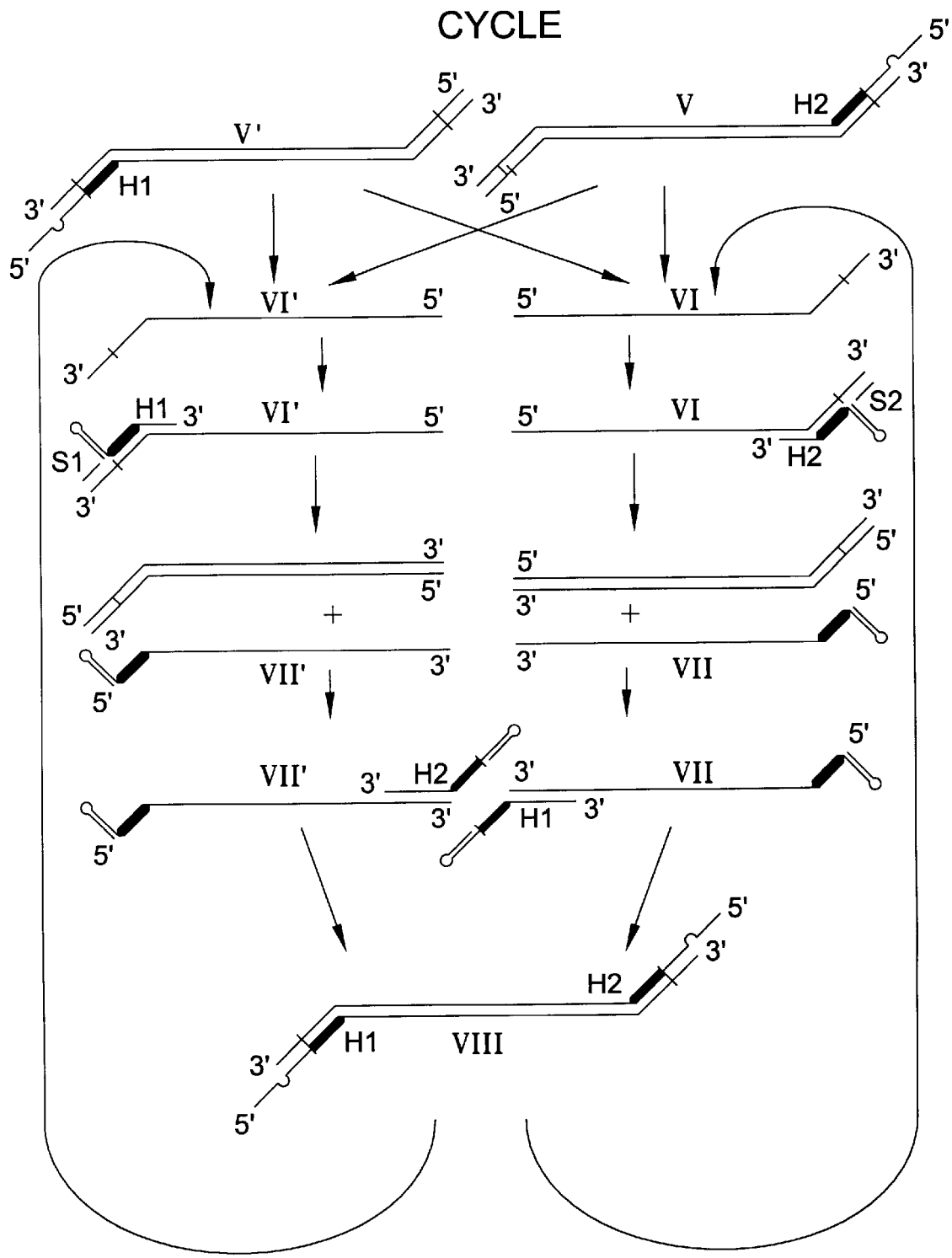

FIGS. 5A and 5B schematically represent another special case of amplification, in accordance with the invention, of nucleic acids using an oligonucleotide comprising a stem-loop structure and containing, in addition, a sense sequence of a promoter for an RNA polymerase. The thin straight lines represent a DNA sequence, the thick lines representing RNA. The highly thickened segment indicates a region containing a sense sequence of a promoter for RNA polymerase. The portion in the form of an arc of a circle represents a structure forming the loop.

Figure 6:
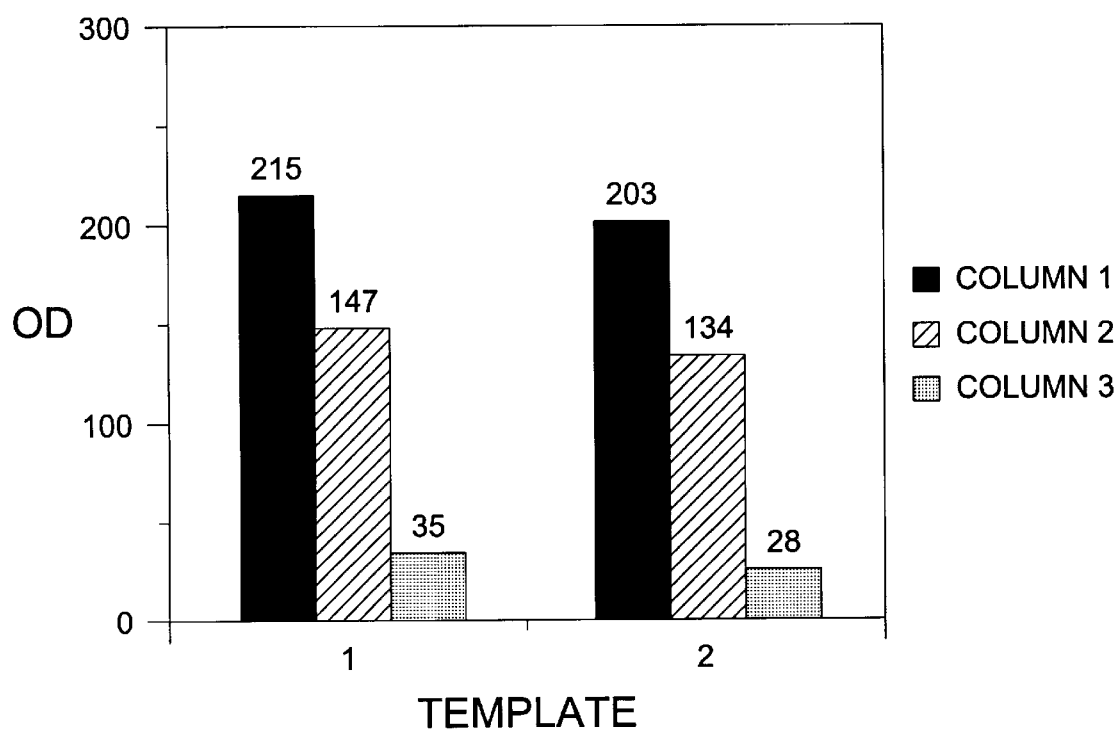

FIG. 6 represents a histogram of the results obtained in accordance with Example 2. The optical density (OD) indicated on the y-axis is given in thousandths. The type of template is indicated on the x-axis: RNA (1) or DNA (2). Column 1 (black) represents the tests in the presence of all the reagents, including reverse transcriptase and the displacement primer. Column 2 (shaded) represents the tests in the presence of all the reagents with the exception of the displacement primer DIS5. Column 3 (shaded grey) represents the tests in the presence of all the reagents with the exception of reverse transcriptase.

Figure 7:
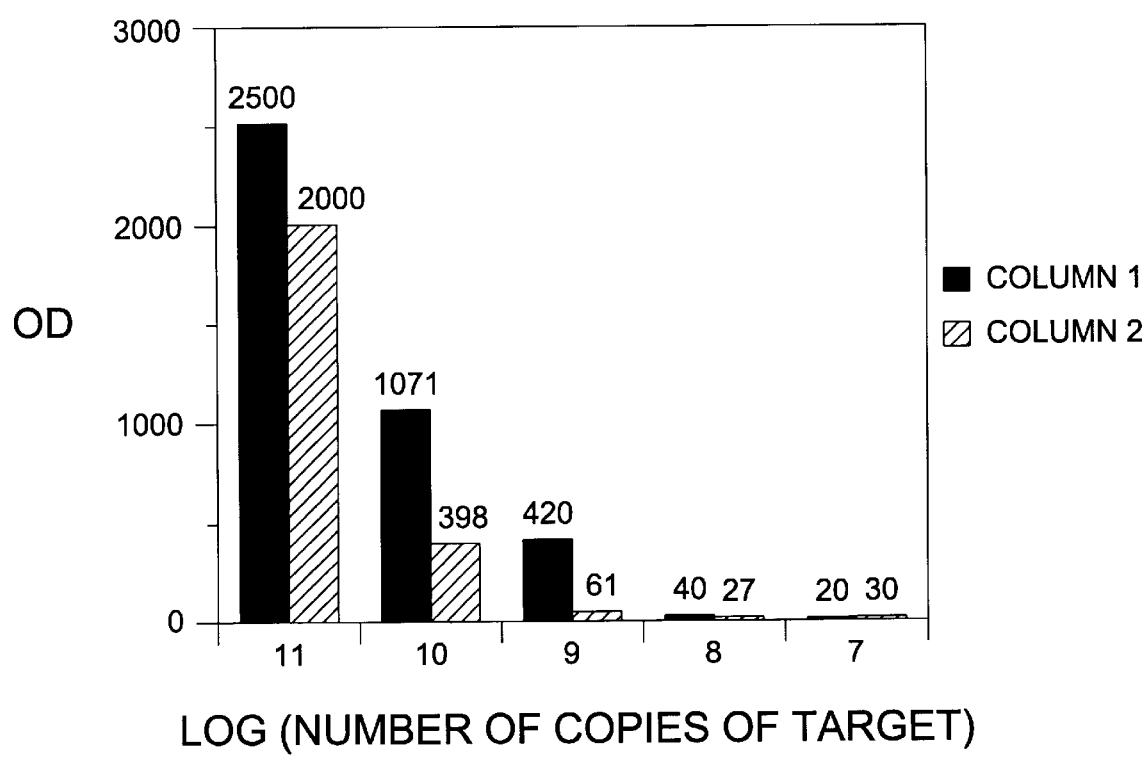

FIG. 7 represents a histogram of the results obtained in accordance with Example 5. The optical density (OD) indicated on the y-axis is given in thousandths. The logarithm of the copy number of target per test is indicated on the x-axis. Column 1 (black) represents the tests in the presence of all the reagents, including reverse transcriptase and the displacement primer. Column 2 (shaded) represents the tests in the presence of all the reagents with the exception of the displacement primers E220 and DIS8.

Figure 8:
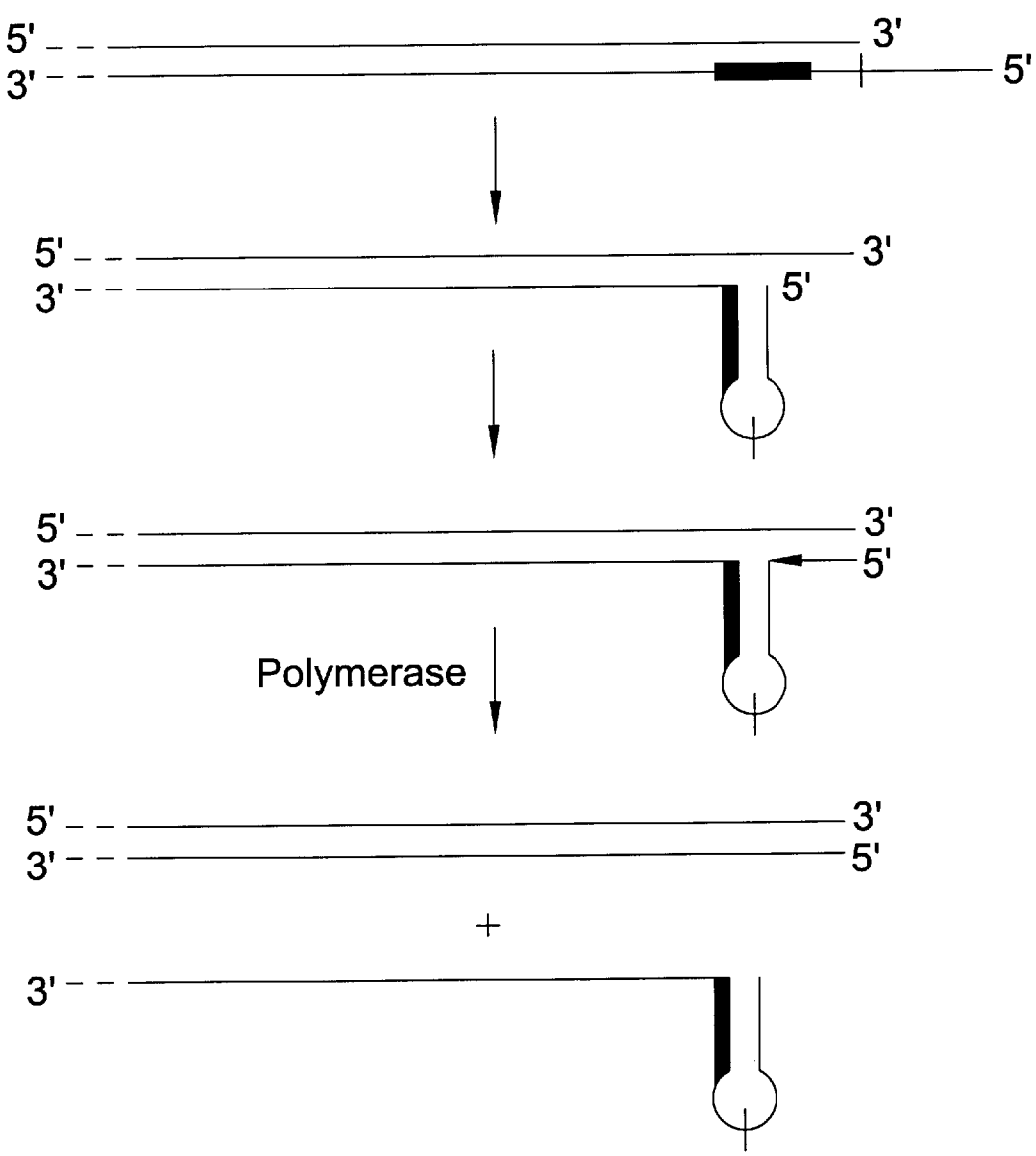

FIG. 8 schematically represents the principle of the study of the displacement of strands containing stem-loop structures within a DNA duplex, with the aid of a DNA polymerase, as described in Example 9. The very thick lines indicate the region of the pin in the stem-loop structure recopied by the polymerase.

Figure 9:
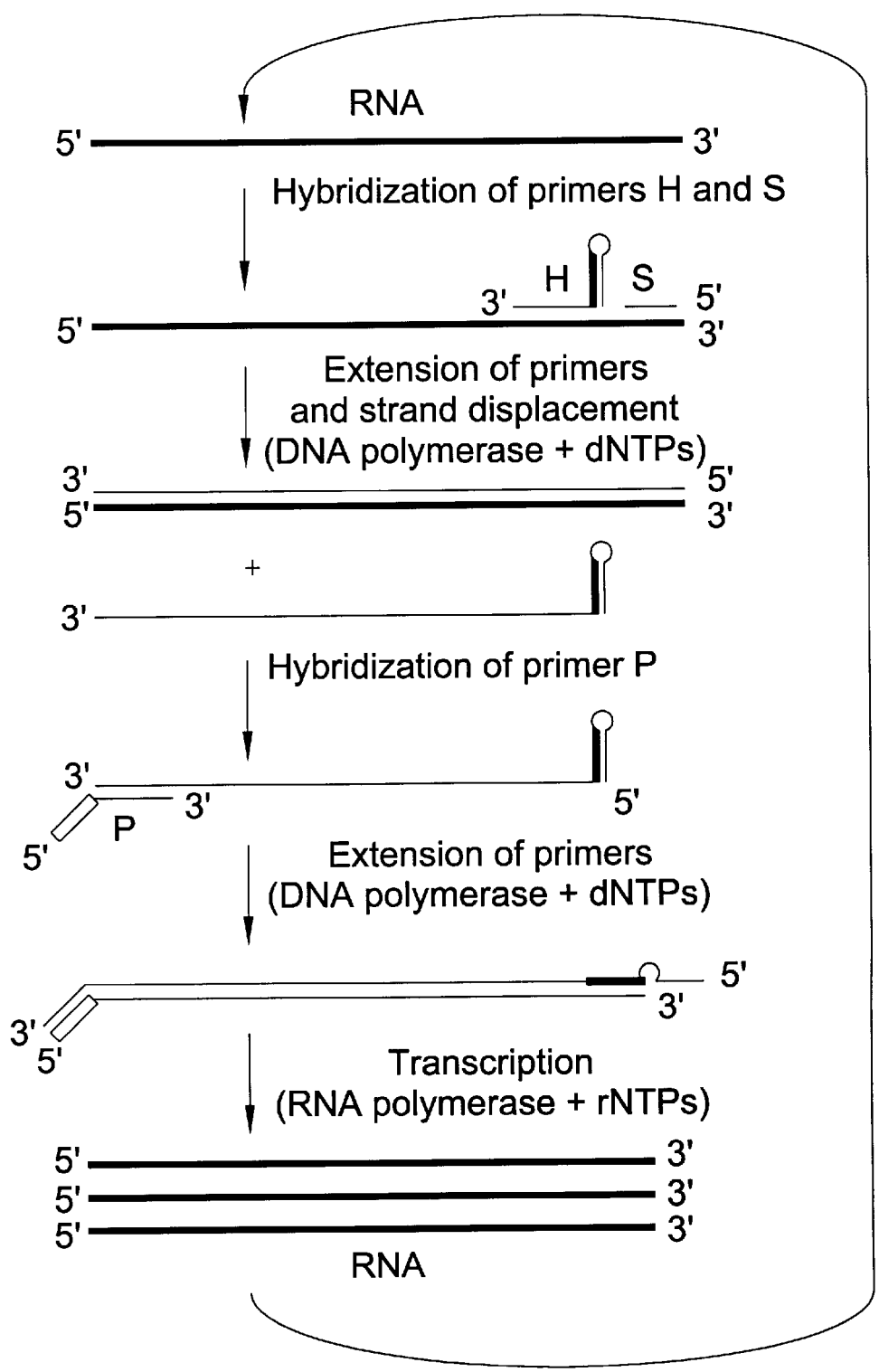

FIG. 9 schematically represents another specific case of amplification, in accordance with the invention, of nucleic acids using an oligonucleotide comprising a stem-loop structure and containing, in addition, a sense sequence of a promoter for an RNA polymerase. The thin straight lines represent a DNA sequence, the thick lines representing RNA. The part in the form of an arc of a circle represents a structure forming the loop.

Figure 10:
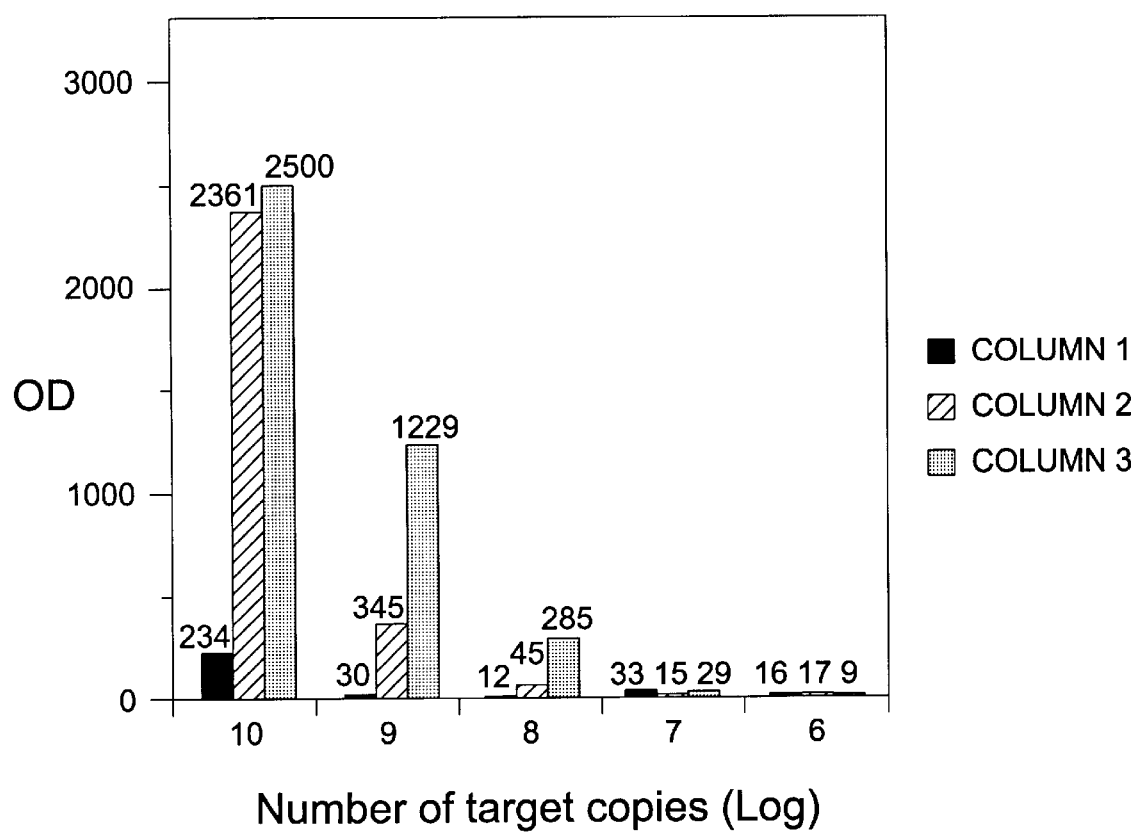

FIG. 10 represents a histogram of the results obtained in accordance with Example 10. The optical density (OD) indicated on the y-axis is given in thousandths. The logarithm of the copy number of target per assay is indicated on the x-axis. Column 1 (black) represents the assays in the presence of all the reagents, with the exception of the enzymes. Column 2 (shaded) represents the assay in the presence of all the reagents with the exception of the displacement primer Dis 22. Column 3 (shaded grey) represents the tests in the presence of all the reagents, including the stem-loop primer.

Figure 11:
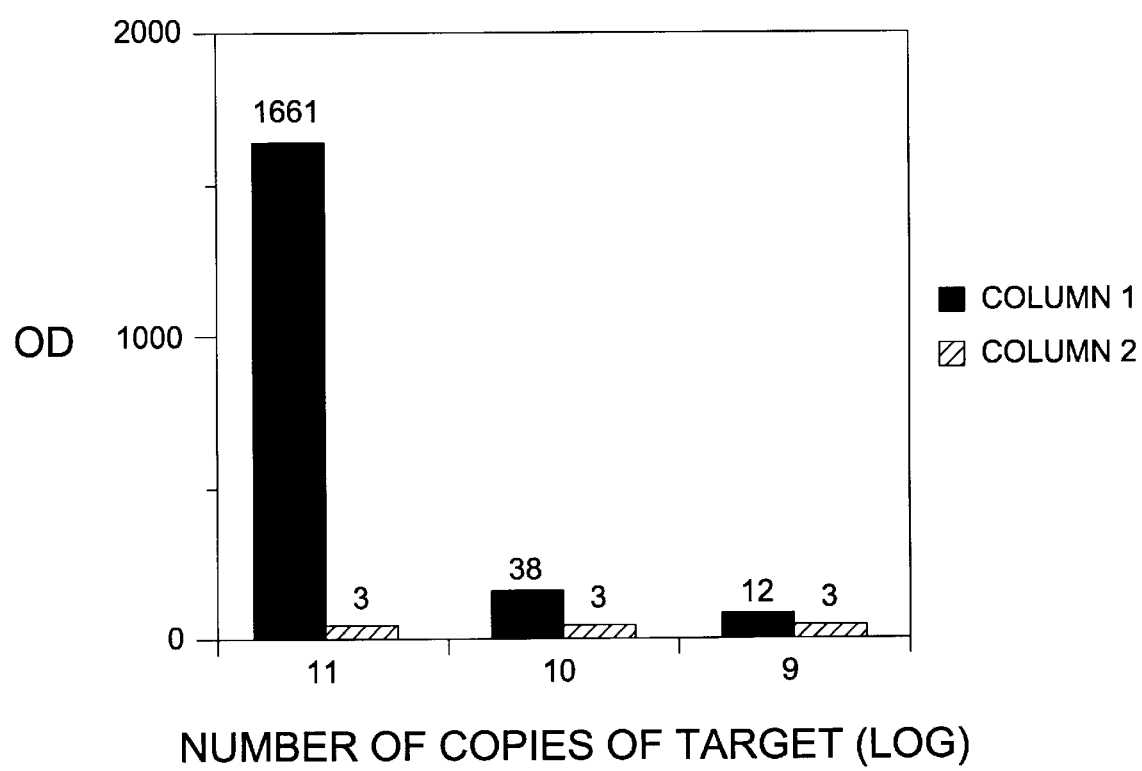

FIG. 11 represents a histogram of the results obtained in accordance with Example 11. The optical density (OD) indicated on the y-axis is given in thousandths. The logarithm of the copy number of target per assay is indicated on the x-axis. Column 1 (black) represents the tests in the presence of all the reagents. Column 2 (shaded) represents the tests in the presence of all the reagents with the exception of the enzyme.

The process which will be described below can operate at constant temperature and especially at the optimum temperature of the DNA polymerase used. Moreover, the primers according to the invention as used for the implementation of this process will be designated in the text which follows by the letter H optionally accompanied by a numbering if several of these primers are involved.

The subject of the present invention is especially an oligonucleotide, as presented in FIG. 1, comprising successively, from its 5' end to its 3' end:

a first portion A, which is at least partially nucleic, comprising from 5' to 3', two nucleic segments (a) and (a') which are self-complementary, capable of self-pairing to form a pin, separated by a third optional and non-obligatory nucleic segment (e) which, when the said pin is formed, may constitute especially an unpaired loop, the whole of the said A portion constituting, in this case, a self-paired molecular structure termed stem-loop, and the said A portion comprising at least one agent blocking extension by a nucleic acid polymerase, a second portion B, of nucleic nature, comprising from 5' to 3', a first optional segment (b) and a second segment (b'), of which at least the said (b') segment is capable of hybridizing with a target nucleic sequence.

Under defined experimental conditions, the (a) and (a') segments combine to form a pin, whereas, if it is present, the (e) segment may constitute especially an unpaired loop; this unit is, in this case, called stem-loop. Of course, it is within the capability of persons skilled in the art to adjust the composition of the (e) segment so that the said segment, when the (a) and (a') segments are self-paired, adopts any structure, other than a loop, regardless of the complexity, the number of loops and/or of pairings involved in the formation of the said structure.

According to the present invention, this A portion of the oligonucleotide comprises at least one agent blocking extension by a nucleic acid polymerase, that is to say an agent capable of blocking the replication or the transcription which should necessarily not extend beyond the 3' end of the region defined by the (a) segment of the said oligonucleotide (FIG. 2) and preferably only the (a') segment will be recopyable. Moreover, the said A portion, which is involved in a duplex with its neosynthesized complementary strand, is capable of forming a molecular structure which is at least partially self-paired following the blocking of the replication or the transcription (FIG. 3).

The (a) and (a') segments are nucleic sequences, DNA and/or RNA, having self-complementarity, that is to say that they are two inverted repeat sequences (relative to the same 5'-3' or 3'-5'axis). Nevertheless, the (a) and (a') sequences may have non-complementary nucleotides insofar as these do not prevent the formation of the said pin. Moreover, each of these (a) and (a') sequences may contain modified nucleotides or non-nucleic components provided that these modifications do not prevent the formation of the said pin.

The (e) segment is optional and comprises either a nucleic sequence, or a non-nucleic structure. The composition of this (e) segment should not inhibit the formation of the stem-loop self-paired structure according to the present invention. If this segment comprises at least one nucleotide sequence, the latter will be chosen so as to exhibit no complementarity with itself, or with the (a) and (a') segments.

In fact, the choice of the components of these (a), (a') and (e) segments is dictated by the need to have at least one agent blocking extension by a nucleic acid polymerase, situated in a region located from the third nucleotide defined from the 3' end of the (a') segment up to the nucleotide of the 3' end of the (a) segment of the said oligonucleotide and preferably in any position of the (e) segment, if the latter is present. In the case where the (e) segment is absent from the oligonucleotide, only the (a') segment or at least a portion of (a') should be recopyable by a nucleic acid polymerase. In this case, the said element blocking polymerization can be located for example at the 3' end of the (a) segment.

This stoppage of replication or of transcription by a polymerase may be obtained by the presence of modified bases non-recopyable by a polymerase, of structures whose sugars are modified, or alternatively of structures capable of hybridizing with nucleic acids but whose nature is different, such as PNAs (Nielsen et al., 1991, Science 254 : 1497–1500; drum et al., 1993, Nucleic acids Res. 21 : 5332–5336). This blocking may also be obtained by inserting arms of hydrocarbon nature such as a hexaethylene glycol arm (Zhang et al., 1991, Nucleic acid Res. 19, 3929–3936) or of a primary aliphatic amine nature (Kessler, 1992, Nonisotopic DNA Probe Techniques, ed. Kricka, Academic Press Inc., New York, pp 58) . Other arms which can be used are described by Uhlmann and Peyman (1990, Chemical Reviews, 90, 544–584). Abasic sites may also be used for blocking the extension (Zhou and Doetsch, 1993, Proc. Natl. acad. Sci. USa 90, 6601–6605). It is also possible to introduce lesions such as cyclobutane-pyrimidine dimers induced by irradiation with ultraviolet rays which are known as RNA polymerase blocking agents.

The production of oligonucleotides according to the invention in a self-paired form is made possible by conditions which make it possible to obtain displacement of the thermodynamic equilibrium from a non-self-paired structure to a stem-loop self-paired structure which, if the loop is of a size which is reduced to zero nucleotide, will constitute a hair-pin structure. These conditions are known or can be determined in each specific case by routine experiments, for example by varying the buffer and temperature conditions. These equilibrium properties have been described in the literature for some specific oligonucleotide sequences (Hirao et al., 1994, Nucleic acids Res. 22 : 576–582; Yoshizawa et al., 1994, Nucleic acid Res. 22 : 2217–2221; Durand et al., 1990, Nucleic acid Res. 18 : 6353–6359). Thus, it has been shown that even very short oligodeoxynucleotides, such as for example d(GCGAAGC), are capable of forming extremely stable hair-pin structures resistant to heat and to nucleases. Moreover, the influence of the sequence on the transition from the non-self-paired form to the oligonucleotide stem-loop self-paired form has been studied (Xodo et al., 1989, Biochemie 71 : 793–803). These authors have thus shown that the folding of the oligonucleotides is not induced by the presence of unpaired nucleotides situated between the inverted repeat sequences because oligonucleotides consisting of the sequence $(^{5'}CG^{3'})_n$ possess a high propensity to form an intramolecular structure. Furthermore, it is the case that the sequences which are least inclined to form stem-loop structures are those whose pin consists of a series of A-T pairings and of G-C pairings at the ends of the loop.

The base composition of the pin is substantially involved in the thermal stability of the pin; in particular, the substitution of a C-G pair by an A-T pair, at the level of the junction of the pin and of the loop, reduces the stability of the structure by 9° C. Other authors have shown the importance of the loop over the stability of the stem-loop structures. Thus, in the case of a loop of 4 nucleotides, this stability is decreased if the $^{5'}C-G^{3'}$ base pair forming the loop is replaced by $^{5'}G-C^{3'}$ whether for DNA or for RNA molecules (Antao and Tinoco, 1992. Nucleic acids Res. 20 : 819–824). The $^{5'}GNRA^{3'}$ type loops are those whose sequence will ensure the best stability of the RNA stem-loop structures. The influence of loops of non-nucleotide nature on the stability of the stem-loop structures has also been studied. In particular, oligodeoxyribonucleotide type structures forming a stem-loop whose loop is a chain obtained from coupling with hexaethylene glycol have been described (Durand et al., 1990, Nucleic acids Res. 18 : 6353–6359).

The length of the loop is also an important factor for the stability of the stem-loop structure. Rentzeperis et al. (1993, Nucleic acids Res. 21 : 2683–2689) have varied the length of a poly-T loop by 3, 5 or 7 nucleotides and thus show that for a given pin, the stability of the structures studied decreases with an increase in the size of the loop. Groebe and Uhlenbeck (1988, Nucleic acids Res. 16 : 11725–11731) have moreover shown that a loop of 4 to 5 nucleotides confers the maximum stability on a stem-loop structure of RNA nature.

In addition, it has been shown that the stem-loop self-paired form is favoured at low ionic strength and in the presence of $MgCl_2$ (Boulard et al., 1991, Nucleic acids Res. 19 : 5159–5167).

As regards the size of the (a), (a') and (e) segments of the oligonucleotides, sizes will for example be chosen varying from 2 to 30 nucleotides, and especially from 3 to 15 nucleotides for the (a) segment and from 2 to 30 nucleotides, and especially from 3 to 15 nucleotides for the (a') segment and from 0 to 20 nucleotides, and especially from 2 to 8 nucleotides for the (e) segment.

The oligonucleotides described in the present application contain a B portion (FIG. 1) located immediately at the 3' end of the (a') segment of the A portion of the said oligonucleotides. This B portion contains successively, from 3' to 5', at least one (b') segment optionally associated with a (b) segment.

The (b) and (b') segments are DNA and/or RNA nucleic sequences. The (b) segment is optional and when it is present, it may especially contain a promoter for an RNA polymerase, a recognition site for a restriction enzyme, an enzyme recognizing a replication origin. The promoter sequences, also called sense or antisense promoter sequences, may especially be promoter sequences for phage RNA polymerases (for example of the bacteriophages T7, T3 or SP6, represented by the sequences SEQ ID No. 19, SEQ ID No. 16 and SEQ ID No. 20, respectively). Moreover, it is known that the T7 phage RNA polymerase requires the presence of a specific promoter on the DNA for an efficient transcription of RNA. The sequence of this specific promoter is perfectly characterized (Dunn and Studier, 1983, J. Mol. Biol. 166 : 477–535) and the high specificity of transcription of T7 RNA polymerase from its promoter has been demonstrated (Bailey et al., 1983, Proc. Natl. acad. Sci. 80 : 2814–2818). These properties may be used in order to produce in vitro RNAs with the aid of T7

RNA polymerase from templates containing a functional double-stranded promoter (Krupp and Sö, 1987, FEBS Lett. 2 : 271–275; Milligan et al., 1987, Nucl. acids Res. 15 : 8783–8798). The article by Krupp (1988, Gene 72 : 75–89) constitutes a good review of the modes of using phage RNA polymerases and of the strategies useful for the synthesis of RNA in vitro. Furthermore, this promoter sequence, when it is present, may be accompanied by a sequence, termed initiation sequence, containing the sequence naturally present near nucleotide +1 on which the initiation of transcription occurs, and located downstream of the T7, T3 or SP6 promoter on the (b) segment. These sequences have the following nucleic and sequences: GGGAGA for T7, GGGAGA for T3 and GAAGGG for SP6.

The (b') segment, for its part, consists of any sequence capable of hybridizing specifically and stably with a given sequence of a target nucleic acid. Although the length of this sequence is not a key factor relating especially to the stability or the properties of the oligonucleotides describe above, it will be possible for the (b') segment to have a length from 5 to 40 nucleotides, and especially from 10 to 20 nucleotides, in order to obtain a rapid, specific and stable hybridization of this (b') segment with a target sequence.

The subject of the present invention is also an oligonucleotide according to the invention which is capable of being used as primer especially in a process for the amplification of a target sequence of a nucleic acid comprising at its 3' end a downstream sequence of at least 5 nucleotides, characterized in that at least the (b') segment of the said oligonucleotide is capable of hybridizing with the said downstream sequence.

The primers according to the present invention make it possible especially to develop a process for the cyclic amplification of a target sequence of a nucleic acid and/or of a sequence complementary to the said target sequence, as indicated above.

This amplification process has the advantages of being isothermal, of being able to use only one enzyme, of being capable of being carried out both from an RNA target and from a DNA target, with or without a defined end, of not being limited by the sequence of the target and of not requiring nuclease activity for the separation of the strands from a duplex or incorporation of modified nucleotides into the amplification products, by the polymerase used.

This method, called "SDR" or "Secondary Structure Displacement Reaction", requires for example the use of a DNA polymerase (RNA or DNA dependent) associated with a strand displacement activity, it being possible for this activity to be provided by the polymerase itself (Masamune and Richardson, 1971, J. Biol. Chem. 246 : 2992–2701; Lundquist and Olivera, 1992, Cell 31 : 53–60).

The polymerase used in the process of the invention is preferably endowed with a strand displacement activity. This activity is a property which is well known for some DNA polymerases (Sambrook et al., 1989, Molecular Cloning : a Laboratory Manual, 2nd Edition, pp. 5.33–5.35, Cold Spring Harbor Laboratory, Cold Spring Harbor). The properties of DNA polymerases, and especially the strand displacement activity of some of them are detailed by Kornberg and Baker (1992, DNA Replication, 2nd Edition, pp. 113–225, Freeman, N.Y.). The strand displacement activity was demonstrated initially for the Klenow fragment of DNA polymerase I of *Escherichia coli* (Masamune and Richardson, 1971, J. Biol. Chem. 246 : 2692–2701) which makes it possible to initiate the replication of a nucleic acid from the 3'OH end of a break in a double-stranded DNA. This strand displacement property is limited in the case where the DNA polymerases have a 5'-3' exonuclease activity (Lundquist and Olivera, 1982, Cell 31 : 53–60). This strand displacement activity has also been demonstrated in thermostable DNA polymerases such as Tli DNA polymerase (Kong et al., 1993, J. Biol. Chem. 268 : 1965–1975). In this case, it was also shown that mutated forms of this enzyme, not having a 5'-3' exonuclease activity possess a greater strand displacement capacity. Strand displacement is not a property common to all DNA polymerases, since some of them, like T4 DNA polymerases, are not capable of carrying out strand displacement on their own. This strand displacement activity has also been demonstrated for T7 DNA polymerase (Lechner et al., 1983, J. Biol. Chem. 258 : 11174–11184) and for HIV reverse transcriptase (Huber et al., 1989, J. Biol. Chem. 264 : 4669–4678). Preferably, a DNA polymerase free of 5'-3' exonuclease activity is used for carrying out the amplification cycle according to the present invention. The Klenow fragment of DNA polymerase I of *Escherichia coli* constitutes an example of polymerase free of 5'-3' exonuclease activity, just as polymerases such as T4 DNA polymerase, T7 DNA polymerase or Sequenase™ (US Biochemical), T5 DNA polymerase or Phi29 DNA polymerase could also be used. Enzymes such as Vent (exo-)™ (New England Biolabs), the Klenow fragment of DNA polymerase I of *Escherichia Coli* (Boehringer Manheim), the Stoffel fragment of Taq polymerase (Applied Biosystems) or Bca DNA polymerase (Takara Shuzo) may also be used. These enzymes have in particular the capacity to carry out the polymerization of nucleic acid from templates having substantial secondary structures, such as stem-loop structures. More particularly, it has been shown that the large fragment of DNA polymerase I of *Bacillus stearothermophilus* has a high capacity to resolve the stem-loop structures (Ye and Hong, 1987, Sci. Sin. 30 : 503–506). The choice of the polymerase used may also vary according to the temperature at which it is desired to work and according to the type of starting nucleic acid (RNA or DNA), in particular, it is possible to use MMLV Reverse Transcriptase Superscript II™, free of RNase H activity (Gibco-BRL) which has a high processing capacity and whose strand displacement capacity was able to be checked, in order to carry out a DNA amplification from an initial RNA target. Any enzyme having an RNA- and/or DNA-dependent DNA polymerase activity can therefore be used in the present invention if it has a strand displacement activity. In the opposite case, the strand displacement activity may be conferred by an inducing agent, a helicase or Rec A type activity. The properties of Rec A, especially in the single-stranded DNA, strand capture or strand assimilation process, are detailed by McEntee and Weinstock (1981, The Enzymes, 14 : 445–470).

Moreover, when at least one of the primers used in the amplification process described above comprises a (b) segment containing the sense sequence of a promoter for an RNA polymerase, it will be possible to combine an RNA polymerase activity with the DNA polymerase and strand displacement activities.

In a specific embodiment, the starting nucleic acid may be a DNA or an RNA extracted from a biological sample for example. In this case, it is possible to obtain an amplification reaction as defined above, starting with the starting nucleic acid, in a single stage by adding all the reagents (primers, polymerases and the like) from the beginning of the reaction, optionally after denaturation of the starting molecule. This specific embodiment is characterized in that in order to obtain the said polynucleotide which is used as starting material in the amplification process, the procedure is carried out starting with a nucleic acid containing the target sequence to be amplified and extending beyond the 5' end of the said target sequence by an upstream region and beyond the 3' end of the said target sequence by a downstream region. In this process, the said starting nucleic acid is placed in contact in the presence of a system with DNA polymerase activity or with DNA and RNA polymerase activities, with strand displacement and with a set of primers containing the primers described above, respectively, and containing, in addition, a fifth primer capable of hybridizing with the downstream region of the starting nucleic acid and/or a sixth primer capable of hybridizing with the upstream region of the starting nucleic acid.

The invention also relates to a set of primers for the cyclic amplification of a target sequence of a nucleic acid and/or a sequence complementary to the said target sequence, the said set comprising:

a first primer H as defined according to the present invention, a second primer S comprising a sequence which is at least partly homologous to the (a') segment of the said primer H.

The amplification method of the invention may be applied to any sample to be analysed which can be isolated from any starting material capable of containing a target nucleic acid sequence. Samples obtained from animals, for example from mammals, may be blood, bone marrow, lymph, hard tissues (liver, spleen, kidney, lungs, ovaries and the like), sputum, faeces, urine. The starting samples may also be obtained from plants, soil samples, foods, as well as any other source suspected to contain biological organisms.

The isolation of the nucleic acids from these starting materials may be carried out according to known processes which comprise especially the use of detergents leading to lysates, the use of enzymes (for example lysozyme or proteinase K for example), ultrasound treatment, mechanical stirring in the presence of beads or the use of a French press. In some cases, it may be necessary to purify the extracted nucleic acids in order to remove possible contaminants such as nucleases. In this case, the purification of the nucleic acids may be carried out for example by phenol-chloroform extraction, chromatography, ion exchange, electrophoresis, equilibrium centrifugation and/or capture by hybridization onto a solid support.

When the nucleic acids are isolated, their rapid fragmentation may be carried out by means such as ultrasound treatment in order to obtain fragments of size less than 20 kilobases. This preliminary stage, which is not imperative, makes it possible to facilitate the initial denaturation in the case especially of a double-stranded nucleic acid. Moreover, the denaturation of the double-stranded nucleic acids, or of the single-stranded nucleic acids having a high secondary structure, may be carried out by a thermal treatment or by increasing the pH and neutralizing the medium, in order to allow the hybridization of the primers according to the invention onto the target sequence.

In the case of the process described in FIGS. 4a–b, the starting nucleic acid, containing especially the target sequence which it is desired to amplify, has been represented in the form of a double strand; however, apart from the initial denaturation stage, the principle remains the same when this nucleic acid is in a single-stranded form.

The process for amplifying, according to the present invention, a target sequence of a starting nucleic acid molecule, the said target sequence comprising at its 3' end a downstream sequence and at its 5' end an upstream sequence, involves:

two primers of the stem-loop type according to the present invention H1 and H2, two displacement primers D1 and D2, two displacement primers S1 and S2.

The primers H1 and H2 are constructed according to the information relating to the above described primers of the present invention. These two primers H1 and H2 comprise successively, from 5' to 3', four types of segments noted (a), (e), (a') and (b'), respectively. The first and third segments (a) and (a') are of nucleic nature and their sequences, although unimportant, have the characteristic feature of being repeated and inverted relative to each other, thus allowing the self-pairing of the (a) segment with the (a') segment and the formation of a pin. The second (e) segment, which is here of nucleic nature and whose sequence is unimportant exhibits no self complementarity and forms a loop when (a) is paired with (a'). In addition, this (e) segment has at its 3' end at least one modified nucleotide or any other molecule which makes it possible to stop the extension reaction by a nucleic acid polymerase. These (a), (a') and (e) sequences may optionally be common to H1 and H2 but may equally well be different. It is evident that the said sequences should not comprise significant homology with the starting nucleic acid and should not give rise to the formation of secondary structures other than the stem-loop self-paired structure as defined above. The fourth (b') segment of the H1 and H2 primers is of nucleic nature and of a different sequence in either of the primers. Indeed, the (b') segment of the H1 primer is complementary to the downstream sequence of the target sequence to be amplified, whereas the (b') segment of the H2 primer is homologous to the upstream sequence of the said target sequence. It is necessary, in addition, to note that when the H1 and H2 primers are introduced into the reaction medium, they exist in their most stable form, that is to say in the stem-loop self-paired form.

The displacement primers D1 and D2 have a size which may vary for example from 5 to 50 nucleotides, and especially from 10 to 35 nucleotides and their sequence is complementary to the sequence situated, on the starting nucleic acid or on its complementary strand, downstream of the sequence which pairs with the (b') segment of the primers H1 and H2, respectively.

The displacement primers S1 and S2 are of a nucleic nature, their size may vary for example from 2 to 30 nucleotides, and especially from 3 to 15 nucleotides and their sequence is homologous to at least a portion of the (a') segment of the primers H1 and H2, respectively. The primers S1 and S2 may, in addition, comprise, upstream of the said sequence, a nucleotide segment containing the sense strand of a promoter for an RNA polymerase, which makes it possible to obtain an additional amplification by formation of transcripts.

After denaturation of the starting nucleic acid, the said primers H1 and D1, on the one hand, and H2 and D2, on the other, are hybridized to the said denatured nucleic acid (strands I and I', respectively) (FIGS. 4a–b). In the presence of a DNA polymerase having a strand displacement activity and dNTP, the extension of the primers D1 and D2 causes strand displacement and the release, into the reaction medium, of the single DNA strands obtained by extension of the primers H1 and H2, respectively. The products thus released (II and II') have, at their 5' end, the sequence corresponding either to the primer H1 or to the primer H2, respectively, and at their 3' end the sequences already present in the starting molecule allowing the hybridization either of the primers H2 and D2 onto the product II, or the primers H1 and D1 onto the product II'. The extension of each of these primers, when they are hybridized, occurs with the release of the strands produced by the extension of the primers H1 and H2. However, when the replication reaches the level of the 5' end of the template (II and II' respectively), the polymerase recopies the sequence of the primers H1 and H2, respectively, previously introduced into these templates. But the synthesis of the DNA strands in progress is stopped at the level of the modified nucleotide(s), or of any other equivalent molecule, initially introduced into the (e) segment of the primer Hi and H2. The products released (IV and IV') therefore have at their 5' end the complete sequence of the primers H1 or H2 and at their 3' end a sequence complementary to the (a') segment of the primer H2 or H1, respectively. As shown in FIGS. 4a–b, these single-stranded polynucleotides IV and IV' thus obtained can hybridize respectively with, on the one hand, the primers H1 and S1 (S1 being homologous to at least a portion of the (a') segment of the primer H1) and with, on the other hand, the primers H2 and S2 (S2 being homologous to at least a portion of the (a') segment of the primer H2). The extension of these primers by DNA polymerase, with displacement, results in the products IV and IV' released by the strand displacement, and in the products V and V' resulting from the extension of the primers S1 and S2 on the templates IV and IV', respectively. The products IV and IV', which are similar in sequence to the products IV and IV' obtained at the preceding stage, may again hybridize with the primers S1 and H1 and S2 and H2, respectively, and lead, as above, to the production of the same reaction products (IV, IV', V and V'). Products V and V' correspond to a double-stranded molecule. They have:

at one of their ends, a duplex formed by a sequence corresponding to the primer S1 or S2, and its complementary strand, at the other end, a duplex formed by a sequence corresponding to the primer H2 or H1, respectively, and strand complementary to the (a') and (b') segments of the said primers.

The products V and V' are obtained here in the form represented by VI and VI', having:

at one of their ends, a duplex formed by the primer S1 or S2 and its complementary strand, at the other end, a stem-loop self-paired structure homologous to that present on the primers 1 or H2. This folding of the double-stranded molecules V and V' makes it possible, in this case, to expose a single-stranded region onto which the displacement primer S2 or S1, respectively, can hybridize.

The extension of the displacement primer S2 or S1 by DNA polymerase is accompanied by the displacement of the paired strand carrying the stem-loop structure. A displaced strand is obtained corresponding to the above described molecule IV or IV' and a molecule VII or VII', corresponding to the target sequence, of the starting nucleic acid which it is desired to amplify. The cyclization of the process appears clearly in FIGS. 4a–b as presented. The amplification occurs at room temperature autocatalytically until depletion of the reagents (enzyme and nucleotides especially) and leads to the accumulation of the products VII or VII'. These amplified products have, in addition, at each of their ends, a sequence corresponding to the co-amplification of at least the portion of the (a') segment of the primer according to the present invention which is capable of pairing with S1 or S2. The presence of this co-amplified fragment may be especially advantageous when it is desired to isolate, purify or detect the amplified target sequence.

The reaction mixture necessary for the carrying out of the amplification according to the invention may especially contain polyols such as glycerol, sorbitol or polyethylene glycol (PEG) or denaturing agents and/or solvents such as dimethylformamide, dimethyl sulphoxide (DMSO) which can make it possible to reduce the nonspecific hybridization reactions capable of generating a background noise. Moreover, the choice of temperature can make it possible to define discriminating hybridization conditions allowing the specific hybridization of the different primers onto their targets and the displacement of the thermodynamic equilibrium between the non-self-paired form and the stem-loop self-paired form (VI and VI') of the products such as the molecules V and V'. This temperature can especially vary from 30° C. to 55° C. with conventional enzymatic reagents and from 60° to 80° C. if thermostable enzymes or reagents are used.

The number of primers used can be advantageously reduced if a pin structure common to the primers H1 and H2 is chosen. In this case, the displacement primers S1 and S2 may be similar. Likewise, some specific cases of the target sequence to be amplified make it possible to choose a displacement primer D1 similar to the displacement primer S1 and a displacement primer D2 similar to the displacement primer S2 and then the displacement primers S1, S2, D1 and D2 may be similar. "Similar" primers refer here either to primers which are identical or to primers having a common sequence (in particular two primers of different lengths of which the longest contains the sequence of the shortest).

In order to increase the efficiency of the amplification system, the primers S1 and S2 may be modified by the addition of a covalently bound intercalating agent (Teiser et al., 1989, J. Am. Chem. Soc. 111 : 7226–7232). This makes it possible to enhance the hybridization of the displacement primers S1 and S2 while not distrupting the extension of the 3' end by a polymerase. Likewise, molecules may be grafted at the 5' end of the primers S1 and S2, as in French Patent No. 91 09057 and in PCT Patent Application No. WO 91 19812, describing the coupling of a protein such as bovine serum albumin. The combination of such sterically bulky molecules at the 5' end of the primers S1 and S2 enhances the formation of the stem-loop self-paired form at the expense of the non-self-paired form of the primers H1 and H2 in the molecules V and V'.

FIGS. 5a–b describes a variant of the method for the amplification of nucleic acids using the primers of the present invention. In this case, a transcription stage is added in order to produce RNA molecules predominantly. To do this, the primers H1 and H2 according to the invention are constructed according to the method described in the technique outlined above, but they contain in addition a (b) segment, located between the (b') segment and the (a') segment, containing a promoter sequence for RNA polymerase, especially a phage promoter (T7, T3 or SP6). In accordance with FIGS. 5a–b, after a series of hybridizations of primers and of extensions accompanied by strand displacement which are analogous to those described in FIGS. 4a–b, the molecules V and V' are obtained in the reaction medium. However, the primers H1 and H2 having especially a (b) segment, the products V and V' have at each of their ends a functional promoter, in the form of a double-stranded DNA. In the presence of an excess of ribonucleoside triphosphates and of an RNA polymerase corresponding to the said promoter, a transcription reaction may be initiated from the said products. The RNAs VI and VI' thus synthesized may hybridize to the primers of the invention H2 and H1 and to the displacement primers S2 and S1, respectively. The displaced products VII and VII' resulting from the extension of the primers H2 and H1, respectively, can hybridize with the primers of the invention H1 and H2, respectively. The extension of these primers with DNA polymerase results, in both cases, in one and the same product VIII. The said product corresponds to the target sequence to be amplified, especially flanked in 5' and in 3' by a functional promoter region, capable of directing the transcription of numerous transcripts, whose sequence corresponds to the RNA molecules VI and VI' obtained above and which can again hybridize with the primers H2 and S2 and H1 and S1, respectively. The RNA derived from one of the two routes of the amplification method described being a substrate for the second, and vice versa, it is therefore apparent that the method according to the invention is a cyclic amplification technique in which the accumulation of the reaction products occurs exponentially.

It is evident that the promoter sequences on the primers of the invention H1 and H2, may be identical or different; however, in this second case, two RNA polymerases are necessary in the amplification reaction. Likewise, it is possible to carry out an amplification of a target nucleic acid sequence using a primer according to the invention which contains a promoter region and a second primer according to the invention not containing one.

The nature and the length of the primers used in this amplification method, the sequence of promoters used and the concentrations of RNA polymerases relative to each type of promoter can be chosen so as to favour one amplification route relative to another, so as to preferably obtain one form or the other of DNA or RNA.

If desired, the amplified products can be separated from the enzymes used for the amplification (DNA polymerase and/or RNA polymerase), so as to be used in subsequent processes involving for example other enzymatic reactions, other amplification systems, sequencing methods or methods for the synthesis of nucleic acids, to mention only a few examples.

Of course, the process of the invention may be followed for example by stages for the separation and/or quantification of the amplification products, it being possible for these stages to be carried out in a manner known per se.

The subject of the invention is also a kit (primers, enzymes) for the detection of a target nucleic acid capable of being present in a sample allowing the implementation of the amplification method described above.

The subject of the invention is also a process for the preparation of an oligonucleotide which can be used especially as primer in a process for the amplification of nucleic acid, characterized in that an oligonucleotide as has been defined in the invention is synthesized according to methods known per se.

The following examples illustrate the invention without however limiting it. Unless otherwise stated, the methods relating to the carrying out of these examples were performed in accordance with their description by Sambrook et al. (1989, Molecular Cloning : A Laboratory Manual, 2nd Edition, Cold Spring Harbor Laboratory, Cold Spring Harbor).

EXAMPLE 1

The oligodeoxyribonucleotides were obtained by solid phase synthesis in an Applied Biosystems synthesizer. The synthesis was carried out using the 2-cyanoethyl N,N-diisopropylamide-phosphite derivatives of the different monomers by following the procedures defined by the manufacturer. All the reagents or solvents used are normally available commercially.

The synthesis of the oligonucleotide chain is carried out starting with a Controlled Pore Glass support of porosity 1000 Å carrying the nucleoside situated in the 3' of the sequence. During the synthesis, the non-nucleotide member (blocking agent) is incorporated using either the amino-Modifier II (Clontech ref: 5203) designated hereinafter N, or the Spacer Phosphoramidite (Clontech Ref: 5260) designated hereinafter N'. The extension of the chain is continued while maintaining the dimethoxytrityl group blocking the 5' hydroxyl functional group of the last nucleoside. The cleavage of the support and the deprotection of the oligonucleotide are performed by treatment with a 33% aqueous solution of ammonia for 12 hours. After addition of a 0.1M solution of triethylamine acetate and concentration of the extension product under reduced pressure, purification is performed by the HPLC technique using a reversed phase column (RPMC $C_8$ 10 ´ 250 mm). The elution is performed with an acetonitrile gradient (Buffer A: 0.1M triethylamine acetate pH: 7; buffer B: 50% buffer A/50% acetonitrile; flow rate 4.7 ml/min from 10% of B to 50% of B over 20 min, spectrophotometric detection at 260 nm) . The different positive fractions are combined and concentrated under reduced pressure. Treatment with an 80% aqueous solution of acetic acid for 30 min at room temperature makes it possible to release the 5' hydroxyl functional group. The acetic acid is evaporated in the presence of ethanol. Ethanol precipitation makes it possible to isolate the desired compound. HPLC analysis is then carried out in order to check the integrity of the products (column RPMC $C_8$ 4.6 ´ 25 mm, flow rate 1 ml/min, from 10 to 14% of B over 18 min, then from 24 to 30% of B over 17 min).

| SEQ. ID. No: | Structure | Retention Time |
| --- | --- | --- |
| 1 | (nucleotide)$_{14}$-N-N-(nucleotide)$_{60}$ | 23.60 |
| 2 | (nucleotide)$_{14}$-N'-(nucleotide)$_{60}$ | 21.35 |
| 3 | (nucleotide)$_{14}$-N-N-(nucleotide)$_{61}$ | 21.16 |
| 4 | (nucleotide)$_{14}$-N'-(nucleotide)$_{61}$ | 21.42 |
| 5 | (nucleotide)$_{14}$-N-N-(nucleotide)$_{30}$ | 20.38 |
| 6 | (nucleotide)$_{14}$-N'-(nucleotide)$_{30}$ | 18.55 |
| 7 | (nucleotide)$_{14}$-N-N-(nucleotide)$_{31}$ | 18.88 |
| 8 | (nucleotide)$_{14}$-N'-(nucleotide)$_{31}$ | 19.28 |

EXAMPLE 2

The strand displacement capacity of a DNA polymerase on a DNA or RNA target in the presence of the stem-loop primers of the present invention was demonstrated by a test in a homogenous phase, that is to say that the single-stranded extension product obtained from the stem-loop primers according to the present invention is detected without denaturation stage, following its displacement by extension of a primer hybridized upstream onto the single-stranded target. The study model chosen is the sequence of the tem gene encoding β-lactamase, an enzyme which confers resistance to the antibiotic ampicilline. The sequence of this gene is described in the sequence SED ID No: 9. This sequence is cloned into the cloning vector pBR322.

In order to analyse the strand displacement capacity of a DNA polymerase on an RNA target, the RNAs corresponding to the sequence of the tem gene (SEQ ID No: 9) were transcribed in vitro, starting with $10^{12}$ copies of double-stranded DNA template, by T7 RNA polymerase, under the reaction conditions recommended in the MEGAscript™ kit (Ambion) . In a first phase, the double-stranded DNA template is synthesized by the Polymerase Chain Reaction (PCR) technique, starting with the clone pBR322, using the primers 1588 (SEQ ID No: 10) and 1562 (SEQ ID No: 11). The 889 base pair product obtained contains especially, at one of its ends, the T7 phage promoter. In the presence of T7 RNA polymerase, an RNA of 867 bases is obtained which corresponds to the sequence complementary to the sequence SEQ ID No: 9. These RNAs are treated with DNase I, purified by phenol/chloroform extraction and ethanol-precipitated in the presence of ammonium acetate salts. The RNAs are taken up in water previously treated with diethyl pyrocarbonate (DEPC), analysed by denaturing polyacrylamide gel electrophoresis and assayed by absorbance at 260 nm. A quantity equivalent to $10^{12}$ copies of target RNA is used per strand displacement assay. In order to carry out the strand displacement assays on a DNA template, an oligonucleotide of 100 bases, called 2585 (SEQ ID No: 12), corresponding to the region complementary to the nucleotides 303 to 402, inclusive, of the sequence SEQ ID No: 9, was chemically synthesized and purified by HPLC.

The displacement assays are carried out in a final volume of 50 ml containing $10^{12}$ copies of target (RNA or DNA), 1 mM DATP, 1 mM dCTP, 1 mM dGTP and 1 mM dTTP (Pharmacia) and 5% glycerol. The reaction mixture also comprises 500 nM of an oligonucleotide primer 2810 (SEQ ID No: 6) corresponding to the primer which it is desired to displace and optionally 500 nM of a displacement primer called DIS5 (SEQ ID No: 13). The reaction mixture is heated for 3 minutes at 65° C. and then preincubated for 10 minutes at 37° C. The enzyme, either 200 U of reverse transcriptase "Superscript$^{II}$" (Gibco-BRL) is added. The reverse transcription reaction is carried out for one hour at 37° C. and then the reaction mixture is frozen at −20° C. A 5 ml fraction is analysed, without denaturation stage, according to the modified capture method and specific ELOSA (Enzyme Linked Oligo Sorbent Assay) detection. This method involves the binding of a capture oligonucleotide onto a solid support (microtitre plate), the hybridization of the displaced-extended product during the reaction onto a capture probe specific for the said product and its visualization using a detection probe coupled to horseradish peroxidase. The capture oligonucleotide A25 (SEQ ID No: 14) is passively bound in the wells of a Nunc-immuno microtitre plate (Maxisorp) according to the method already described in French Patent No. 91 09057, allowing the binding of about 5 pmol of oligonucleotide onto a well. After binding, three washes are carried out with 1×PBS Twin buffer. The detection of the captured displacement product is performed in accordance with the technique described in French Patent No. 91 09057. The 5 ml fraction to be analysed is added to a volume of 45 ml of 0.2M sodium phosphate buffer pH 7, 1M sodium chloride, 2 mM EDTA, 1.3% SDS, 0.24 mg/ml salmon DNA, 4% polyethylene glycol (PEG) 6000. Each sample is deposited into the well of a microtitre plate treated with the capture probe A25 (SEQ ID No: 14), as described above. Immediately afterwards, 50 ml of 0.2M sodium phosphate buffer pH 7, 1M sodium chloride, 2 mM EDTA, 1.3% SDS, 0.24 mg/ml salmon DNA, 4% polyethylene glycol (PEG) 6000, containing 5 ng of detection oligonucleotide probe A28 (SEQ ID No: 15), coupled to horseradish peroxidase, are added. After incubating for 60 minutes at 37° C., the wells are washed with 1×PBS Tween. The visualization of the A28-peroxydase probe hybridized onto the displaced product is performed by adding 100 ml of a solution containing the substrate ortho-phenylenediamine (OPD). The calorimetric reaction is stopped after 20 minutes by the addition of 100 ml of 1M sulphuric acid. The optical density at 492 nm is read by means of an AXIA microreader (BioMérieux).

The results obtained are presented in FIG. 6. They show, on the one hand, that the presence of a displacement primer (SEQ ID No 13) makes it possible to obtain a substantial release, into the medium, of the strand derived from the extension of the displaced primer (oligonucleotide 2810), whether on a DNA or RNA template. In the absence of displacement primer, the signal corresponding to the extension of the primer 2810 is about twice as small. This demonstrates the efficiency of the strand displacement on the RNA or DNA template using the reverse transcriptase Superscript$^{II™}$. These results can in addition be quantified, thereby making it possible to show that this reverse transcriptase, free of RNase H activity, has a greater efficiency for the displacement of a DNA strand on an RNA template than on a DNA template.

EXAMPLE 3

This example is intended to show that the templates containing a stem-loop self-paired structure upstream of a promoter sequence can be transcribed by an RNA polymerase. This type of template was synthesized, from pBR322, by the PCR technique using the oligonucleotides 2801 (SEQ ID No: 1) and 1028 (SEQ ID No: 18), on the one hand, and 2806 (SEQ ID No: 2), and 1028 (SEQ ID No: 18) on the other, in the presence of the Stoffel fragment of Taq polymerase (Applied Biosystems), free of 5'-3' exonuclease activity. The absence of this exonuclease activity makes it possible to eliminate the possible degradation of the pin portion of the stem-loop structures of the present invention during the different PCR cycles necessary for the synthesis of the said templates. The PCR products obtained (templates), analysed on a 3% Nusieve agarose gel (FMC), have an apparent molecular weight of 130 base pairs. They contain, downstream of a stem-loop self-paired structure, the promoter for the T7 phage RNA polymerase (SEQ ID No: 19). The bands corresponding to these products are cut out of the agarose gel and the PCR products are electroeluted. They are ethanol-precipitated in the presence of sodium acetate and assayed at 260 nm. The transcription assays are carried out at 37° C. for two hours in a final volume of 50 ml, in the reaction buffer described by Milligan et al. (1987, Nucl. Acids Res. 15 : 8783–8798), in the presence of ATP, CTP, GTP and UTP (4 mM each, Boehringer), 1 U/ml of RNA guard (Pharmacia), 1 U/ml of T7 RNA polymerase (New England Biolabs) and $10^{11}$ copies of purified PCR template.

A fraction of the reaction mixture (10 ml) is mixed with 10 ml of a 0.035% xylene cyanol, 0.035% bromophenol blue, 1 mM EDTA, 98% formamide solution before being analysed by denaturing polyacrylamide gel electrophoresis containing 15% acrylamide, 7M urea, 0.26% bisacrylamide, 90 mM Tris-borate, 2 mM EDTA, pH 8.3. These gels are poured into mini-protean II electrophoresis cell™ electrophoresis apparatus (Biorad) and they have a thickness of 1 mm. Before being deposited on the gel, the samples are denatured at 65° C. for 2 minutes and rapidly cooled on ice. The electrophoresis is carried out at 150 volts, until the bromophenol blue runs to 1 cm from the bottom of the gel. The gels are stained for 10 minutes in an ethidium bromide solution at 0.6 mg/ml and photographed on a UV table (312 nm) by means of an MP4 apparatus (Polaroid).

The products separated by electrophoresis are transferred onto Hybond N™ nylon membrane (Amersham) by means of a mini trans-blot electrophoretic transfer cell™ apparatus (Biorad), in a 45 mM Tris-borate buffer, 1 mM EDTA, pH 8.3, at 4° C., in an electric field of 35 volts.hour$^{-1}$.cm$^{-1}$. The membranes are dried for 5 minutes at 80° C. and the nucleic acids are fixed on the membrane by exposing to UV radiation (312 nm) for 3 minutes.

These membranes are prehybridized at 37° C. for 60 minutes in 4 ml of 0.1M sodium phosphate buffer pH 7.0, 0.5M sodium chloride, 1 mM EDTA, 0.65% SDS, 0.14 mg/ml salmon DNA, 2% polyethylene glycol 6000 (PEG). The hybridization is carried out by incubating for 60 minutes at 37° C. in 5 ml of the same buffer containing, at the concentration of 200 ng/ml, the oligonucleotide A28 (SEQ ID No: 15) labelled with horseradish peroxidase by coupling in 5' according to the process described above in International Patent No. WO 91/19812. After 3 washes of 30 seconds in 50 ml of 1×PBS buffer (Sambrook et al., 1989, Molecular Cloning: A Laboratory Manual, 2nd Edition, Cold Spring Harbor Laboratory, Cold Spring Harbor) containing 0.05% of Tween 20, the hybridized oligonucleotide is visualized by the activity of the peroxidase in the presence of 10 mg of diaminobenzidine tetrahydrochloride dihydrate (DAB) in 20 ml of 20 mM sodium phosphate buffer pH 7.2, 150 mM sodium chloride, 2 mg/ml bovine serum albumin. After incubating at room temperature and protected from light for 15 minutes, the reaction is stopped by rinsing with distilled water.

A control for T7 RNA polymerase activity was previously made up by preparing a double-stranded DNA fragment by PCR, from a target pBR322, with the aid of the primers A24 (SEQ ID No: 17) and 1028 (SEQ ID No: 18). The 285 base pair product thus obtained contains, at one end, the T7 phage promoter and its transcription by T7 RNA polymerase makes it possible to obtain an RNA of 263 bases. The control for the T7 RNA polymerase activity is produced by incubating $10^{11}$ copies of the 285 base pair fragment under the conditions described above. This reaction is carried out for two hours at 37° C., in parallel with the transcription assays on the templates containing the stem-loop structures of the present invention.

The results obtained confirm the capacity of the templates containing a stem-loop self-paired structure upstream of a promoter for RNA polymerase to be transcribed in vitro. The nature of the loop does not appear to have any influence since the templates containing a loop with two aminoModifier II™ residues (amino included in the primer 2801; SEQ ID No: 1) or a Spacer Phosphoramidite™ residue (polyethylene glycol included in the primer 2806; SEQ ID No: 2) make it possible to obtain the transcript of the expected size with an identical yield in both cases.

EXAMPLE 4

The stem-loop primers of the present invention should be partially recopyable by a nucleic acid polymerase. For this purpose, several DNA polymerases were tested: thermostable enzymes such as Taq polymerase (Applied BioSystems), the Stoffel fragment of Taq polymerase (Applied BioSystems), Bca polymerase (Takara), Vent™ polymerase (New England Biolabs) and thermostable enzymes such as Klenow fragment (Boehringer), the reverse transcriptase Superscript™ (Gibco-BRL) and T4 DNA polymerase (New England Biolabs). These polymerases were tested for their capacity to extend a primer on a template consisting of stem-loop oligonucleotides according to the present invention, as well as on a control template 2799 (SEQ ID No: 21), not containing a structure of this type. The primer A26 (SEQ ID No: 22), complementary to the 3' end of these templates, was labelled with the isotope $^{32}P$ at its 5' end with T4 polynucleotide kinase in the presence of [g-$^{32}P$] ATP. The labelled primer was purified by filtration on a Sephadex G25 gel (Pharmacia) and the equivalent of 10 pmol of labelled primer, corresponding to $2 \times 10^7$ cpm, is hybridized with 20 pmol of template, in the commercially available buffer corresponding to the enzyme (final volume 20 ml). The enzyme is added (3 U of T4 DNA polymerase, or 200 U of reverse transcriptase or 5 U of Klenow, or 1 U of thermostable polymerase) and then incubated for one hour at 37° C. for the thermophilic enzymes and at 50° C. for the thermostable enzymes. The reactions are stopped by freezing at −20° C. The products are then analysed by denaturing acrylamide gel electrophoresis. The gels are formed by polymerization of a solution containing 20% acrylamide, 7M urea, 0.26% bisacrylamide, 90 mM Tris-borate, 2 mM EDTA, pH 8.3 and are poured into electrophoresis apparatus The Sturdler™ (Hoefer Scientific Instruments) of a thickness of 1 mm. The samples to be analysed are prepared by mixing 10 ml of reaction mixture and 10 ml of a 0.035% xylene cyanol solution, 0.035% bromophenol blue, 1 mM EDTA, 98% formamide. Before depositing on the gel, these samples are denatured at 95° C. for 2 minutes and then rapidly cooled on ice. The electrophoresis is carried out at 450 volts, until the bromophenol blue runs to 1 cm from the bottom of the gel. The gels are dried on Whatman 3MM paper and subjected to autoradiography for 2 hours. The size of the extension products is determined relative to a molecular weight marker consisting of different oligonucleotides labelled in 5' like the primers, deposited on the gel in parallel.

Analysis shows a complete extension of the primer on the control template SEQ ID No. 21, in the presence of the different types of enzymes used, leading to an extension product of 59 bases. On the templates 2801 (SEQ ID No. 1) and 2804 (SEQ ID No. 21), extension products of 60 and 30 bases are obtained, respectively, in the presence of the enzymes Stoffel, Superscript™, Vent™ and Klenow. These products correspond to an extension of the primers on the targets comprising the stem-loop self-paired structures up to the last base preceding the chemical modification amino-Modifier II™. This demonstrates, on the one hand, that the stem-loop self-paired structure thus formed may be opened by virtue of the strand displacement activity of these enzymes, and that these stem-loop self-paired structures are only partially recopyable because of the presence of the chemical modification since the replication of these structures is stopped by the said modification. Likewise, results of the same nature are obtained on the templates 2806 (SEQ ID No. 2) and 2810 (SEQ ID No. 6) since extension products of 60 and 30 bases are obtained, respectively, in the presence of the enzymes Stoffel, Superscript$^{II}$™, Vent™ and Klenow. These products correspond to the extension of the primer A26, on targets comprising stem-loop self-paired structures, up to the last base preceding the chemical modification Spacer Phosphoramidite™. The use of the enzymes Taq and Eca does not make it possible to obtain the expected extension products regardless of the type of stem-loop structure used. Given that these enzymes possess an exonuclease activity (5'-3'), it is probable that they degrade the template even before they have been able to recopy it. It is useful to note, in the case where T4 DNA polymerase is used, that no extension product is observed in the presence of the templates 2804 and 2810, and that on the other hand, an extension product of about 50 nucleotides is obtained in the presence of the templates 2801 and 2806. This appears to indicate that T4 DNA polymerase is not capable of opening, in order to copy them, the stem-loop structures used in the present example.

EXAMPLE 5

An amplification is carried out according to the method described in FIGS. 5a–b. For that, a 167 base pair fragment was synthesized by the PCR technique by means of the primers DTA7 (SEQ ID No: 23) and DTA8 (SEQ ID No: 24), from pBR322, and which therefore contains a portion of the sequence of the tem gene corresponding to the nucleotides 336 to 402, inclusive, of SEQ ID No: 9. This fragment contains, at each of its ends, a promoter sequence for RNA polymerase (in particular the T7 phage promoter), preceded in 5' by a sequence homologous to the sequence E220 (SEQ ID No: 25). In order to demonstrate the exponential nature of the method, different amplification reactions were carried out in parallel in the presence of decreasing quantities of target molecule consisting of the preceding purified PCR fragment: from $10^{11}$ to $10^7$ copies per assay. The reactions are carried out in a final volume of 50 ml, in the presence of ATP, CTP, GTP and UTP (4 mM each), of dATP, dCTP, dGTP and dTTP (1 mM each), of 1 U/ml of T7 phage RNA polymerase (New England Biolabs), of 4 U/ml of MMLV Superscript$^{IIT\text{M}}$ reverse Transcriptase (Gibco-BRL), free of Rnase H activity, and 1 U/ml of RNA guard (Pharmacia). The reaction medium contains, in addition, the primers H1 and H2 according to the invention corresponding to the oligonucleotides 2806 and 2808 (SEQ ID No: 2 and SEQ ID No: 4, respectively) at a concentration of 1 mM and the displacement primers E220 (SEQ ID No: 25) and S1 (or S2) corresponding to the oligonucleotide DIS8 (SEQ ID No: 26) at a concentration of 0.1 mM. After incubating for two hours at 37° C., the amplification reactions are stopped by freezing the reaction medium at −20° C. A 5 ml fraction, that is to say ⅒th of the reaction volume is quantitatively analysed by capture and specific detection according to the ELOSA (Enzyme Linked Oligo Sorbent Assay) method. The method involves the binding of a capture oligonucleotide onto a solid support (microtitre plate), the denaturation of the reaction product, its hybridization onto the capture probe specific for the amplified sequence and visualization using a detection probe coupled to horseradish peroxidase. The capture oligonucleotide A20 (SEQ ID No: 27) is passively bound to the wells of a Maxisorp Nunc-immuno microtitre plate according to the method already described in French Patent No. 91 09057, allowing the binding of about 5 pmol of oligonucleotide onto a well. After binding, three washes with 1×PBS Tween buffer are carried out. The detection of the captured amplification product is performed in accordance with the technique previously described in French Patent No. 91 09057. The 5 ml fraction to be analysed is added to a volume of 35 ml of 0.2M sodium phosphate buffer pH 7.0, 1M sodium chloride, 2 mM EDTA, 1.3% SDS, 0.24 mg/ml salmon DNA, 4% polyethylene glycol (PEG) 6000. The nucleic acids contained in this sample are denatured by adding 5 ml of 2M sodium hydroxide at room temperature, and neutralized after 3 minutes by adding 5 ml of 2M acetic acid. For control and calibration, two series of dilution of RNA corresponding to the expected amplification products are performed. Each sample is then deposited in the well of a microtitre plate in which the capture oligonucleotide probe A20 (SEQ ID No: 27) has been bound beforehand. Either 50 ml of undiluted sample, or the same volume of sample diluted ⅒th or ¹⁄₁₀₀th, are deposited. Immediately, a volume of 50 ml of 0.2M sodium phosphate buffer pH 7.0, 1M sodium chloride, 2 mM EDTA, 1.3% SDS, 0.24 mg/ml salmon DNA, 4% polyethylene glycol (PEG) 6000, containing 5 ng of detection oligonucleotide probe A19 (SEQ ID No: 28) coupled to horseradish peroxidase, is added. After incubating for 60 minutes at 37° C., the wells are washed with 1×PBS Tween. The visualization of the A19-peroxidase probe hybridized onto the amplification product is performed by adding 100 ml of a solution containing the substrate ortho-phenylenediamine (OPD). The colorimetric reaction is stopped after 20 minutes by adding 100 ml of 1M sulphuric acid. The optical density at 492 nm is read by means of an AXIA microreader (BioMérieux). The results obtained are represented by the histograms in FIG. 7. For each of the dilutions of target, two assays were performed: complete assay (as described above) and assay without displacement primer E220 and DIS8. The results show that the amplification method (complete system) makes it possible to detect, under these conditions, a significant specific signal up to an initial target quantity of $10^8$ copies per assay, that is to say a sensitivity of $10^7$ copies, since a fraction equivalent to ⅒th of the reaction medium is analysed under these conditions. This sensitivity is only relative and can be greatly increased if a visualization system other than colorimetry (for example fluorescence, chemiluminescence or bioluminescence) is used. The results show in particular that in the absence of displacement primer E220 and DIS8, a specific signal is obtained only for a target quantity equal to $10^9$ copies per assay. The difference in detection sensitivity between "with" and "without" displacement primer is therefore of a factor $10^2$, or of 2 units Log of base 10. This demonstrates that the method allows substantial accumulation of amplification product, it being possible for the latter to come only from the carrying out of the amplification cycle. The carrying out of the cycle is therefore possible only in the presence of the displacement primers. These data show that the method is based on the cyclization of the process up to the transcription stage by means of an enzymatic displacement stage, in particular with the aid of a displacement primer in the presence of a DNA polymerase such as a reverse transcriptase. Qualitative analysis of the amplification assays by electrophoretic separation, transfer onto a nylon membrane and hybridization, as described in Example 3, with the aid of the probe A28 (SEQ ID No: 15), on the one hand, and of the probe A19 (SEQ ID No: 28) on the other, coupled to horseradish peroxidase, made it possible to detect two complementary RNA molecules of 110 bases, corresponding to the expected amplification product.

EXAMPLE 6

In order to demonstrate the capacity of various non-nucleotide arms to block polymerization, several types of stem-loop primers were synthesized (according to the technique described in Example 1) : some containing a non-nucleotide arm Aminomodifier II™ (Clontech ref: 5203) comprising 2 (3116; SEQ ID No: 30) or 4 carbons (2804; SEQ ID No: 5), the others containing an arm Spacer Phosphoramidite™ (Clontech ref: 5260) containing 12 carbons (2810; SEQ ID No: 6) or an α-thymidine nucleoside, designated adT, 3531 (SEQ ID No: 32) (the phosphoramidite required for the incorporation of the nucleoside is prepared from the commercial nucleoside Sigma ref: T3763) . The stoppage of polymerization along these special stem-loop structures was analysed with several polymerases: a) thermostable enzymes such as the Stoffel fragment of Taq polymerase (Applied Biosystems) or 9°Nm™ (New England Biolabs) and b) thermolabile enzymes such as the Klenow fragment of polymerase I of *Escherichia coli* (Boehringer) or the reverse transcriptase Superscript II™ (Gibco BRL).

In a first instance, the primer A26 (SEQ ID No: 22) which is complementary to the 3' end of each of the templates was labelled at its 5' end with T4 polynucleotide kinase in the presence of [g-$^{32}$P]ATP, then purified by filtration on a Sephadex G-25 gel (Pharmacia). In a second instance, $10^{12}$ copies of stem-loop primers (SEQ ID No: 30, 5, 6, or 29) and $10^{12}$ copies of labelled oligonucleotide A26 (SEQ ID No: 22) are mixed in the presence of each of the dNTPs (1 mM final) in a reaction volume of 20 ml (commercial buffer (1×final) corresponding to each of the enzymes which it is desired to use) and in the presence of 200 U of reverse transcriptase, 50 U of Klenow fragment, 1 U of Stoffel fragment of Taq polymerase, or 2U of 9°Nm. After incubation for one hour at 37° C., the reactions are stopped by freezing at −20° C. and the products are analysed by denaturing polyacrylamide gel electrophoresis, as described in Example 4. The size of the extension products is determined relative to a molecular weight marker consisting of various oligonucleotides labelled in 5' and deposited in parallel on the gel.

The results obtained show that the extension of the primer A26 is interrupted by the non-nucleotide arm on the templates consisting of the stem-loop structure 2804 (SEQ ID No: 5), 2810 (SEQ ID No: 6), 3239 (SEQ ID No: 31) and 3531 (SEQ ID No: 29) when the replication is carried out with the Klenow fragment; on the templates consisting of the stem-loop structure 2810 (SEQ ID No: 6), 3239 (SEQ ID No: 31) and 3531 (SEQ ID No: 29) when the replication is carried out with reverse transcriptase; on the templates consisting of the stem-loop structure 2804 (SEQ ID No: 5), 2810 (SEQ ID No: 6), 3116 (SEQ ID No: 30), 3239 (SEQ ID No: 31) and 3531 (SEQ ID No: 29) when the replication is carried out with the Stoffel fragment. The use of stem-loop structures comprising a polyethylene glycol non-nucleotide arm of 12 carbons (Spacer Phosphoramidite), for example the structures 2810 (SEQ ID No: 6) and 3239 (SEQ ID No: 31), is an advantageous solution for carrying out the present invention because it does not allow polymerization beyond the non-nucleotide site, regardless of the enzyme used. It appears, in addition, that there is a relationship between the length and/or the nature of the non-nucleotide arm and the capacity to stop the polymerase by this element and by a given enzyme.

EXAMPLE 7

In order to demonstrate the capacity of a double-stranded DNA fragment to form a stem-loop structure according to the invention, a double-stranded DNA fragment of 135 base pairs was synthesized. For that, part of the tem gene (SEQ ID No: 9) included in the plasmid pBR322 was amplified by the PCR technique with the aid of the stem-loop primer 3336 (SEQ ID No: 32), which contains a non-nucleotide arm of the AminoModifier II™ type, and of the primer 1863 (SEQ ID No: 36) in the presence of the Stoffel fragment of Taq polymerase (Applied Biosystems) lacking 5'-3' exonuclease activity. The fragment obtained contains, at one of the 5' ends, a sequence capable of forming a stem-loop structure. In parallel, a control PCR is carried out in the presence of the primer 3215 (SEQ ID No: 39) and the primer 1863 (SEQ ID No: 36). The PCR amplification product thus obtained contains only the sequence of the pin and constitutes a molecular weight marker of 135 base pairs in duplex form.

After PCR, the products are analysed on a 2% SeaKem LE agarose gel (FMC). After migration at 80 V for 2 hours in a 1×TBE buffer solution (89 mM Tris-HCl pH 8.3, 89 mM boric acid, 2 mM EDTA), the gel is stained in the presence of ethidium bromide (0.6 mg/ml) . Analysis of the PCR products shows two bands of different size corresponding to two forms of migration of the products obtained from the stem-loop primer 3336 (SEQ ID No: 32) and only one form of migration in the case of the molecular weight marker. The two forms of electrophoretic mobility visualize two different conformations, stem-loop or duplex, of one of the 5' ends of the DNA fragment. The form with the fastest electrophoretic migration corresponds to a molecule in which the sequence of the primer 3336 introduced into the PCR fragment exists in duplex form, the form with the slowest electrophoretic migration corresponds to a molecule in which the said sequence of the primer 3336 is folded in the form of a stem-loop.

The bands observed on agarose gel are cut out and purified with the aid of a gel extraction kit Qiaex II™ (Qiagen, ref: 20021). The purified products are deposited on a 2% SeaKem LE agarose gel (FMC) under conditions identical to those described above. The migration of the product corresponding to the rapid form leads to a single band which migrates in an identical manner to that derived from the purification of the product of the control PCR. The product corresponding to the slow form previously isolated leads to the obtaining of a single band which is slowed down in relation to that derived from the purification of the control PCR.

In order to confirm that the two bands obtained on agarose gel correspond to two isomeric forms of the same PCR amplification product, each of the bands previously isolated and purified from the product of this PCR was sequenced with the aid of a Dye Deoxy Terminator cycle sequencing kit (Applied Biosystems). The sequencing reaction requires a first amplification carried out using $10^{11}$ copies of the purified product in the presence of 10 ml of sequencing reaction mixture and 5 ml of the primer 1863 (SEQ ID No: 39) from the initial PCR.

The sequencing reaction is carried out in a Thermocycler 480 apparatus (Perkin Elmer) according to the following cycle: 30 seconds at 96° C., 15 seconds at 40° C. and 4 minutes at 60° C., the whole repeated 25 times. This PCR product is then purified on a Sephadex G-50 column (Pharmacia), then sequenced on an automatic sequencer (Applied Biosystems 373 A).

Analysis of the results shows that there is no difference between the sequences obtained from the product of the control PCR, of the rapid form or of the slow form which were purified above. Moreover, the sequence conformity between, on the one hand, the product of the control PCR and, on the other hand, the two isolated isomeric forms confirms that the pin part of the stem-loop structure is replicated accurately by the Stoffel fragment of Taq polymerase. This replication is interrupted, as previously demonstrated in Example 6, by the non-nucleotide part of the loop of the primers of the present invention.

These elements as a whole show that the incorporation of a primer capable of forming a stem-loop type secondary structure, according to the present invention, allows the formation of two isomeric forms comprising, at their end, the same sequence either in the form of a stem-loop or in the form of a duplex.

EXAMPLE 8

Displacement assays (according to the model of FIG. 9) were carried out on an RNA transcribed from the PCR amplification product of 572 base pairs previously obtained with the primers 2434 (SEQ ID No: 10) containing a T7 phage promoter at its 5' end, and 3239 (SEQ ID No: 31) having a Spacer Phosphoramidite™ (hexaethylene glycol) residue. This RNA has, at its 3' end, a sequence complementary to the pin part of the primer 3239, allowing the hybridization of a displacement primer Dis-22 [g-$^{32}$P]ATP (SEQ ID No: 40). This RNA can, in addition, hybridize with the stem-loop primer A21 (SEQ ID No: 37) at its 3' end. A reaction control is produced by substituting the stem-loop primer 3239 by the primer 3215 (SEQ ID No: 39) which has the pin sequence upstream (5') of the sequence A21. The displacement reactions are carried out in a final volume of 20 ml in the presence of reverse transcriptase Superscript II™ (GIBCO-BRL) in the buffer optimized by the supplier, dNTPs (1 mM each, Pharmacia), $10^{11}$ copies of target per assay and 5 ' $10^{12}$ copies of primer per assay. After incubation for 30 minutes at 37° C., the reactions are stopped by adding 20 ml of 0.02% xylene cyanol buffer, 0.02% bromophenol blue, 25 mM EDTA, 90% formamide. The samples are denatured at 65° C. for 3 minutes, cooled rapidly on ice and analysed by electrophoresis on an 8% denaturing polyacrylamide gel (7M urea) in TBE buffer (90 mM Tris-borate, 2 mM EDTA, pH 8.3). The electrophoresis is carried out at 300 V until the tracking dye is about 1 cm from the bottom of the gel.

A control of the extension of the stem-loop primer 3239 (SEQ ID No: 31) by reverse transcriptase on the RNA template, in the presence of the displacement primer Dis 22 (SEQ ID No: 40) is carried out in which the primer 3239 (SEQ ID No: 31) labelled in 5' with [g-$^{32}$P]ATP is incubated, under the conditions presented above, in the presence of the unlabelled displacement primer Dis 22 (SEQ ID No: 40). Electrophoresis confirms that the stem-loop structure is recopied up to the 5' end of the RNA template. Likewise, the hybridization and the extension of the displacement primer Dis 22 (SEQ ID No: 40) on the synthesized RNA template is checked by incubating this primer labelled in 5' with [g-$^{32}$p]ATP. This extension allows the synthesis of a cDNA whose length is compatible with the RNA template. Moreover, the intensity of the product visualized reflects the degree of folding of one of the 5' ends of the molecules produced, in a stem-loop form.

The displacement assays show a product of extension of the displacement primer on an RNA template, confirming the displacement of the strand derived from the extension of the stem-loop primer used. This tends to prove that the stem-loop primer used, when it is hybridized to the RNA template, is present in a folded stem-loop form, thus allowing the displacement primer to hybridize to the 3' part of the RNA. When the displacement assays are carried out by replacing the primer 3239 (stem-loop) with the primer 3215 (absence of stem-loop structure), the low intensity of the product of extension of the displacement primer confirms that the pin sequence contained in the primer 3215 prevents the hybridization of the displacement primer, by a phenomenon of competition at the level of the same hybridization site. The stem-loop primer studied in this particular case shows that the stability of this stem-loop structure is superior to that of the corresponding DNA/RNA heteroduplex which could form by displacement of the thermodynamic equilibrium. These results demonstrate the possibility of using stem-loop primers according to the present invention on an RNA template.

The effect of an acridine-type intercalating agent attached to the 5' end of a stem-loop primer on the strand displacement efficiency on an RNA template was also studied. For this purpose, an RNA template was transcribed from a PCR product containing the primer 3215 (SEQ ID No: 39) and the promoter primer 2709 (SEQ ID No: 38). The displacement assays are carried out on an RNA template as described above, in the presence of a displacement primer Dis 22 (SEQ ID No: 44) labelled in 5' with [g-$^{32}$p]ATP.

The tests are carried out according to two different methods. According to a first method, the cDNA derived from the extension of the stem-loop primers studied is preformed in the presence of suitable reagents (reverse transcriptase, nucleotides), and the displacement primer is added to the reaction mixture at an interval of 15 minutes; according to a second method, the analysis is carried out, as above, with all the reagents present in the reaction medium at the same time. In both methods, the reaction products are incubated for 30 minutes at 37° C.

Two stem-loop primers were studied: 3221 (SEQ ID No: 33) and 3516 (SEQ ID No: 35), the latter corresponding to the primer 3221 with an acridine group (6-chloro-2-methoxyacridine—Clontech ref 5236) situated at its 5' end. A displacement control consists of the primer A21 (SEQ ID No: 37). The primers, without any distinction, are at a concentration of 5 ' $10^{12}$ copies per assay, and the RNA template used is at $10^{11}$ copies per assay. Analysis of the products is carried out by electrophoresis on an 8% denaturing polyacrylamide gel as described above. Extension products of the same intensity are obtained from the control prepared with the primer A21, with or without the preforming stage, confirming the absence of competition at the level of this system. The carrying out of the preforming stage in the case of the stem-loop primer 3221 (SEQ ID No: 32) does not lead to the production of a product of extension of the displacement primer, whereas the same assay, carried out without a preforming stage, gives a positive result as described above. Signals of the same intensity are obtained using the primer 3516 (SEQ ID No: 35), with or without a preforming stage. The intensity of this signal is identical to that obtained using the primer 3221 without preforming.

These results show that the presence of an acridine-type intercalating group at the 5' end of the primer studied allows the formation of the stem-loop structure by intermolecular folding, within a long preformed RNA:DNA heteroduplex. In the absence of acridine, the RNA:DNA duplex form associated with the corresponding stem-loop appears to be predominant, since no displacement signal is observed. These results show the value which the presence of an intercalating agent on the primers may have in order to promote the intermolecular folding of the stem-loop structures.

EXAMPLE 9

PCR amplification products were synthesized under the conditions described above, with the aid of the primer 1863 (SEQ ID No: 36), and of one of the following primers: the stem-loop primer 3514 (SEQ ID No: 34) having an acridine group in 5' and a non-nucleotide arm Spacer hexaethylene glycol (Clontech ref 5260), or the stem-loop primer 3239 (SEQ ID No: 31) containing a phosphoramidite spacer arm, but no acridine group, or the control primer 3215 (SEQ ID No: 39) containing a pin sequence but no stem-loop structure. The amplification products are purified as described above.

Assays of displacement of the stem-loop structure were carried out, according to the principle described in FIG. 8. $10^{11}$ copies of purified PCR target are mixed at 37° C. with the commercial buffer for the Klenow fragment of DNA polymerase I of *Escherichia coli* in the presence of dNTPs (1 nM) and displacement primer Dis 9 (SEQ ID No: 41), whose sequence is identical to that of the pin of the stem-loop structure. This oligonucleotide is labelled in 5' with [g-$^{32}$p]ATP. The final reaction volume is 20 ml.

The tests are carried out with or without initial thermal denaturation (3 minutes at 95° C.). 5U of Klenow fragment of DNA polymerase I of *Escherichia coli* are added. After 1 hour at 37° C., the reactions are stopped by freezing and the extension products are analysed by electrophoresis on a denaturing polyacrylamide gel. The products are visualized by autoradiography.

The results reveal extension products of an expected size of 141 bases in the presence of PCR amplification templates synthesized from the primers 3215, 3239 and 3516, when the assays are carried out after thermal denaturation. Without a stage for thermal denaturation of the target beforehand, an extension product of expected size is obtained for the PCR amplification templates synthesized with the stem-loop primers 3516 and 3239, but no product is detected in the case of the PCR carried out with the primer 3215 (negative control). These elements show that the presence of a stem-loop structure within a DNA duplex makes it possible, by folding of the said structure, to release a single-stranded site which can then hybridize with a displacement primer. This primer may then be extended and may displace the strand situated downstream, containing a stem-loop structure at its 5' end (FIG. 8). In the absence of a stem-loop structure (case of the primer 3215), the double-stranded form of the template prevents the hybridization of any displacement primer for hybridization.

EXAMPLE 10

Amplification tests according to the technique described in FIG. 9 were carried out. A target of 83 base pairs was synthesized by the PCR technique with the aid of the primers 3215 (SEQ ID No: 39) and 2709 (SEQ ID No: 38), from the plasmid pBR322. This target contains, at a 5' end, the promoter sequence for T7 phage RNA polymerase and, at the other 5' end, the sequence of the pin contained in the stem-loop primer used in the amplification tests. The target is used under conditions of decreasing concentration ranging from $10^{10}$, $10^9$, $10^8$, $10^7$ and $10^6$ copies. The reaction medium (25 ml) contains the stem-loop primer 3514 (SEQ ID No: 34) containing a hexaethylene glycol group as well as an acridine in 5', and the promoter primer 2709 (SEQ ID No: 38) at a final concentration of 1 mM. The displacement primer Dis 22 (SEQ ID No: 40), whose sequence is identical to the sequence of the pin contained in the stem-loop primer, is used at 1 mM final. The reaction buffer used is that optimized by Milligan et al. for the activity of the T7 RNA polymerase, supplemented with 50 mM potassium glutamate and contains rNTPs (Pharmacia) (4 mM) and dNTPs (Pharmacia) (1 mM). The enzymes used are 50 U of T7 RNA polymerase (Biolabs) or 200 U of reverse transcriptase Superscript II™ (GIBCO BRL). For each of the target dilutions, three assays were carried out: a complete assay (as described above), an assay without displacement primer Dis 22, and a test without enzymes. After an incubation of two hours at 37° C., the amplification reactions were stopped by freezing the reaction medium to −20° C. ⅕th of the reaction volume is analysed quantitatively by capture and specific detection according to the ELOSA method. The technique for attachment of the capture oligonucleotide A20 (SEQ ID No: 27), as well as the detection of the captured amplification product is described in Example 5 above. The fraction of 5 ml to be analysed is added to a volume of 35 ml of polyethylene glycol (PEG). The nucleic acids contained in this sample are denatured by adding 5 ml of 1M sodium hydroxide. Each sample is deposited in the well of a microtitre plate in which the capture probe A20 (SEQ ID No: 27) has been previously attached. The addition of the detection probe A19 (SEQ ID No: 28), the incubation and the reading of the microplate are carried out in accordance with the technique described above in FIGS. 5a–b.

The results obtained (FIG. 10) show that the amplification method makes it possible to detect a significant specific signal up to an initial target quantity of $10^8$ copies per assay, that is to say an absolute sensitivity of 2 ′ $10^7$ copies, since a fraction equivalent to 1/5th of the reaction medium is analysed under these conditions. In the absence of the displacement primer Dis 22, a significant specific signal is obtained up to an initial target quantity of $10^9$ copies per assay, that is to say an absolute sensitivity of 2 ′ $10^8$ copies. These results demonstrate the possibility of obtaining an accumulation of amplification product by cyclization of the process in the presence of the displacement primer. In the absence of enzyme, the sensitivity of detection is $10^{10}$ copies per assay.

EXAMPLE 11

The use of the stem-loop primers of the present invention in an amplification method as described in FIGS. 4a–b, was studied. PCR products of 91 base pairs, comprising at each end stem-loop structures with a phosphoramidite non-nucleotide arm, were used as amplification target. They were synthesized with the aid of the primers 2810 (SEQ ID No: 6) and 2811 (SEQ ID No: 8). These same primers were used at a concentration of 1 mM final in the amplification assays; the displacing oligonucleotide Dis 9 used (SEQ ID No: 41) is labelled in 5' with [g-$^{32}$P]ATP and used at a final concentration of 1 mM. The amplifications are carried out on dilutions of target ranging from $10^{11}$ to 0 copies of target per assay, in the presence of 5 U of Klenow fragment of DNA polymerase of *Escherichia coli* (Boehringer), in the commercial buffer recommended for this enzyme, and in the presence of 1 mM dNTPs (Pharmacia) . The tests are carried out in a total volume of reaction medium of 50 ml and incubated for 3 hours at 37° C. A control test without enzyme was also carried out under the same conditions.

¹⁄₁₀th of the reaction volume is analysed quantitatively by capture and specific detection according to the ELOSA method. The detection of the amplification product is performed with the aid of the capture oligonucleotide A25 (SEQ ID No: 14) and the detection probe A28 (SEQ ID No: 15), according to the method described in Example 5.

Analysis of the results obtained (FIG. 11) shows that a significant amplification signal is obtained under these experimental conditions, for initial target quantities of $10^{11}$ and $10^{10}$ copies per test, that is to say an absolute sensitivity of $10^9$ copies, since a fraction equivalent to ¹⁄₁₀th of the reaction medium is analysed under these conditions. In the absence of enzyme, no significant signal is obtained, the starting target is not even detected. Given the specificity of detection of the ELOSA method, these results show that a specific accumulation of product occurs.

We claim:

1. Oligonucleotide comprising successively, from its 5' end to its 3' end,
   a first portion capable of self-pairing in order to form a stem-loop structure comprising an upstream segment and a downstream segment which are paired, and
   a second portion not capable of self-pairing,
   wherein said first portion comprises at least one blocking agent capable of blocking the replication, by a polymerase, of said oligonucleotide, such that at least a portion of the downstream segment is replicated and such that the upstream segment is not replicated totally or partially.

2. Oligonucleotide according to claim 1, wherein the blocking agent is such that the portion of the downstream segment capable of being replicated has a length of at least 2 nucleotides.

3. Oligonucleotide according to claim 1, wherein the downstream end of the upstream segment and the upstream end of the downstream segment are linked by a loop.

4. Oligonucleotide according to claim 1, wherein said upstream and downstream segments each contain from 2 to 30 nucleotides.

5. Oligonucleotide according to claim 1, wherein said first portion comprises, as the blocking agent, either a hydrocarbon arm or a modified nucleotide which, when present in an oligonucleotide template for a polymerase, stops replication and transcription by said polymerase at the level of said modified nucleotide.

6. Oligonucleotide according to claim 1, wherein the oligonucleotide contains, between said first and second portions, a third portion containing a sense sequence of a promoter for an RNA polymerase.

7. Oligonucleotide according to claim 1, wherein said second portion contains from 5 to 40 nucleotides.

8. Oligonucleotide primer that can be used in a process for the amplification of a target sequence of a nucleic acid, said target sequence comprising a downstream region of at least 5 nucleotides, said oligonucleotide primer comprising an oligonucleotide as defined in claim 1, wherein said second portion contains, at its 3' end, a sequence capable of hybridizing with said downstream region of the target.

9. Process for cyclic amplification of a target sequence of a nucleic acid, said target sequence comprising, at its 5' ends an upstream region and, at its 3'end, a downstream region, said process comprising the steps of:

(1) obtaining a single-stranded polynucleotide comprising a first segment corresponding to the target sequence to be amplified, a second segment situated upstream of the 5' end of the first segment and a third segment situated downstream of the 3' end of the first segment, wherein said second segment of said single-stranded polynucleotide is capable of self-pairing in order to form a stem-loop structure comprising an upstream segment and a downstream segment which are paired, and said third segment of said single-stranded polynucleotide has any sequence, (2) exposing said polynucleotide to:

(a) a first primer as defined in claim 8, capable of hybridizing with the downstream region of the target sequence, wherein at least a downstream portion of the downstream segment of the first portion of the first primer is complementary to the third segment of the single-stranded polynucleotide, (b) optionally a second primer as defined in claim 8, capable of hybridizing with a downstream region of a sequence complementary to the target sequence, said downstream region being complementary to said upstream region of the target sequence, wherein the first portion of the second primer is a homologue of the second segment of said single-stranded polynucleotide, (c) a third primer whose sequence is homologous to at least a downstream portion of a sequence of the downstream segment of said first portion of the first primer, (d) a fourth primer whose sequence is homologous to at least a portion of a sequence of the downstream segment of said second segment of said single-stranded polynucleotide, and (e) an enzymatic system having at least an activity for replicating said nucleic acid and a strand displacement activity, and (3) incubating a mixture obtained in step (2) under conditions allowing hybridization to occur and the enzymatic activities to function.

10. Process according to claim 9, wherein said first primer is an oligonucleotide comprising successively, from its 5' end to its 3' end, a first portion capable of self-pairing in order to form a stem-loop structure comprising an upstream segment and a downstream segment which are paired, a second portion not capable of self-pairing, and between said first and second portions, a third portion containing a sense sequence of a promoter for an RNA polymerase, wherein said first portion comprises at least one blocking agent capable of blocking the replication, by a polymerase, of said oligonucleotide, such that at least a portion of the downstream segment is replicated and such that the upstream segment is not replicated totally or partially, wherein said single-stranded polynucleotide contains, between said first segment and said third segment, a fourth segment complementary to said sense sequence contained in the first primer, and wherein said enzymatic system further contains an RNA polymerase activity under the control of the promoter corresponding to the sense sequence.

11. Process according to claim 9, wherein said polynucleotide is exposed to the second primer and said second primer is an oligonucleotide comprising successively, from its 5' end to its 3' end, a first portion capable of self-pairing in order to form a stem-loop structure comprising an upstream segment and a downstream segment which are paired, a second portion not capable of self-pairing, and between said first and second portions, a third portion containing a sense sequence of a promoter for an RNA polymerase, wherein said first portion comprises at least one blocking agent capable of blocking the replication, by a polymerase, of said oligonucleotide, such that at least a portion of the downstream segment is replicated and such that the upstream segment is not replicated totally or partially, wherein said single-stranded polynucleotide contains, between said first segment and said second segment, an additional segment whose sequence is the same as the sense sequence contained in the second primer, and wherein said enzymatic system further contains, an RNA polymerase activity under the control of the promoter corresponding to the sense sequence contained in the second primer.

12. Oligonucleotide according to claim 2, wherein the downstream segment capable of being replicated has a length of at least 3 nucleotides.

13. Oligonucleotide according to claim 4, wherein said upstream and downstream segments each contain from 3 to 15 nucleotides.

14. A process according to claim 10, wherein the blocking agent is such that the portion of the downstream segment capable of being replicated has a length of at least two nucleotides.

15. A process according to claim 9, wherein the downstream end of the upstream segment and the upstream end of the downstream segment are linked by a loop.

16. A process according to claim 9, wherein said upstream and downstream segments each contain from 2 to 30 nucleotides.

17. A process according to claim 10, wherein said first portion comprises, as the blocking agent, either a hydrocarbon arm or a modified nucleotide which, when present in an oligonucleotide template for a polymerase, stops replication and transcription by said polymerase at the level of said modified nucleotide.

18. A process according to claim 9, wherein the downstream segment capable of being replicated has a length of at least 3 nucleotides.

19. A process according to claim 9, wherein said upstream and downstream segments each contain from 3 to 15 nucleotides.

* * * * *